United States Patent
Harris et al.

(10) Patent No.: US 10,729,434 B2
(45) Date of Patent: *Aug. 4, 2020

(54) SURGICAL STAPLER WITH INSERTABLE DISTAL ANVIL TIP

(71) Applicant: ETHICON LLC, Guaynabo, PR (US)

(72) Inventors: Jason L. Harris, Lebanon, OH (US); Ryan Bledsoe, Cincinnati, OH (US); Joseph P. Schowalter, South Lebanon, OH (US); Gregory J. Bakos, Mason, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 336 days.

This patent is subject to a terminal disclaimer.

(21) Appl. No.: 15/435,607

(22) Filed: Feb. 17, 2017

(65) Prior Publication Data

US 2018/0235610 A1     Aug. 23, 2018

(51) Int. Cl.
*A61B 17/072* (2006.01)
*A61B 17/28* (2006.01)
*A61B 17/00* (2006.01)

(52) U.S. Cl.
CPC ...... *A61B 17/072* (2013.01); *A61B 17/07207* (2013.01); *A61B 2017/00477* (2013.01);
(Continued)

(58) Field of Classification Search
CPC ........ A61B 17/072; A61B 2017/08221; A61B 2017/08257; A61B 2017/08271;
(Continued)

(56) References Cited

U.S. PATENT DOCUMENTS 4,633,861 A * 1/1987 Chow .............. A61B 17/07207
227/153
4,805,823 A   2/1989 Rothfuss
(Continued)

FOREIGN PATENT DOCUMENTS

EP    2 314 230 A1    4/2011
EP    2 777 523 A1    9/2014
(Continued)

OTHER PUBLICATIONS

U.S. Appl. No. 15/435,573, filed Feb. 17, 2017.
(Continued)

*Primary Examiner* — Chelsea E Stinson
*Assistant Examiner* — Himchan "Aiden" Song
(74) *Attorney, Agent, or Firm* — Frost Brown Todd LLC

(57) ABSTRACT

A surgical instrument includes a body, a shaft, and an end effector that is operable to compress, staple, and cut tissue. The end effector includes and anvil and a cartridge. The anvil has a body and a modular releasable curved tip that connects with the body. The curved tip is elastically deformable in response to force exerted on the curved tip when tissue is clamped between the anvil and cartridge. The curved and deformable features of anvil provide for an end effector with improved visualization and maneuverability, in particular during procedures involving marching. The modular nature of the curved anvil tip provides for an end effector that allows anvil tip replacement due to wear or interchangeability based on a user preference or procedure.

20 Claims, 17 Drawing Sheets

(52) U.S. Cl.
CPC .............. *A61B 2017/00738* (2013.01); *A61B 2017/00862* (2013.01); *A61B 2017/07221* (2013.01); *A61B 2017/07257* (2013.01); *A61B 2017/07271* (2013.01); *A61B 2017/2825* (2013.01)

(58) Field of Classification Search
CPC .......... A61B 2017/07221; A61B 2017/07257; A61B 2017/07271; A61B 2017/00477; A61B 2017/2946; A61B 2017/2933–2937
USPC .......................................... 227/175.1–182.1
See application file for complete search history.

(56) References Cited

U.S. PATENT DOCUMENTS

| | | | |
|---|---|---|---|
| 5,389,098 A * | 2/1995 | Tsuruta | A61B 17/00234 606/41 |
| 5,415,334 A | 5/1995 | Williamson et al. | |
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitma et al. | |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,783,524 B2 * | 8/2004 | Anderson | A61B 34/70 606/28 |
| 6,978,921 B2 | 12/2005 | Shelton et al. | |
| 7,000,818 B2 | 2/2006 | Shelton et al. | |
| 7,143,923 B2 | 12/2006 | Shelton et al. | |
| 7,303,108 B2 | 12/2007 | Shelton | |
| 7,367,485 B2 | 5/2008 | Shelton et al. | |
| 7,380,695 B2 | 6/2008 | Doll et al. | |
| 7,380,696 B2 | 6/2008 | Shelton et al. | |
| 7,404,508 B2 | 7/2008 | Smith et al. | |
| 7,434,715 B2 | 10/2008 | Shelton et al. | |
| 7,524,320 B2 | 4/2009 | Tierney et al. | |
| 7,644,848 B2 | 1/2010 | Swayze et al. | |
| 7,691,098 B2 | 4/2010 | Wallace et al. | |
| 7,721,930 B2 | 5/2010 | McKenna et al. | |
| 7,806,891 B2 | 10/2010 | Nowlin et al. | |
| 8,136,711 B2 * | 3/2012 | Beardsley | A61B 17/07207 227/175.1 |
| 8,210,411 B2 | 7/2012 | Yates et al. | |
| 8,403,196 B2 * | 3/2013 | Beardsley | A61B 17/07207 227/175.1 |
| 8,408,439 B2 | 4/2013 | Huang et al. | |
| 8,453,914 B2 | 6/2013 | Laurent et al. | |
| 8,479,969 B2 | 7/2013 | Shelton | |
| 8,573,461 B2 | 11/2013 | Shelton et al. | |
| 8,573,465 B2 | 11/2013 | Shelton | |
| 8,602,288 B2 | 12/2013 | Shelton et al. | |
| 8,616,431 B2 | 12/2013 | Timm et al. | |
| 8,783,541 B2 | 7/2014 | Shelton et al. | |
| 8,800,838 B2 | 8/2014 | Shelton | |
| 8,820,605 B2 | 9/2014 | Shelton | |
| 8,844,789 B2 | 9/2014 | Shelton et al. | |
| 9,186,142 B2 | 11/2015 | Fanelli et al. | |
| 9,301,759 B2 | 4/2016 | Spivey et al. | |
| 9,333,003 B2 * | 5/2016 | Kappel | A61B 17/29 |
| 9,517,065 B2 | 12/2016 | Simms et al. | |
| D833,010 S | 11/2018 | Harris et al. | |
| 2004/0243151 A1 * | 12/2004 | Demmy | A61B 17/105 606/139 |
| 2007/0114261 A1 * | 5/2007 | Ortiz | A61B 17/064 227/175.1 |
| 2008/0269793 A1 * | 10/2008 | Scirica | A61B 17/07207 606/190 |
| 2011/0155780 A1 * | 6/2011 | Boudreaux | A61B 17/068 227/175.2 |
| 2011/0226837 A1 * | 9/2011 | Baxter, III | A61B 17/072 227/175.1 |
| 2012/0241492 A1 * | 9/2012 | Shelton, IV | H05K 999/99 227/175.1 |
| 2012/0248169 A1 * | 10/2012 | Widenhouse | A61B 17/105 227/175.1 |
| 2013/0075449 A1 * | 3/2013 | Schmid | A61B 17/00491 227/176.1 |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239041 A1 | 8/2014 | Zerkle | |
| 2014/0239042 A1 * | 8/2014 | Simms | A61B 17/07207 227/176.1 |
| 2014/0239043 A1 * | 8/2014 | Simms | A61B 17/07207 227/176.1 |
| 2014/0239044 A1 | 8/2014 | Hoffman | |
| 2014/0263572 A1 * | 9/2014 | Shelton, IV | A61B 17/068 227/180.1 |
| 2015/0209030 A1 * | 7/2015 | Kostrzewski | A61B 17/068 227/177.1 |
| 2015/0209037 A1 * | 7/2015 | Kostrzewski | A61B 17/0682 227/178.1 |
| 2015/0272575 A1 | 10/2015 | Leimbach et al. | |
| 2017/0224343 A1 * | 8/2017 | Baxter, III | A61B 17/32 |
| 2019/0076143 A1 * | 3/2019 | Smith | A61B 34/30 |

FOREIGN PATENT DOCUMENTS

| | | |
|---|---|---|
| EP | 2 913 010 A2 | 9/2015 |
| WO | WO 2013/151888 A1 | 10/2013 |

OTHER PUBLICATIONS

U.S. Appl. No. 15/435,618, filed Feb. 17, 2017.
U.S. Appl. No. 15/435,631, filed Feb. 17, 2017.
U.S. Appl. No. 29/594,332, filed Feb. 17, 2017.
U.S. Appl. No. 29/594,340, filed Feb. 17, 2017.
European Search Report and Written Opinion dated May 4, 2018 for Application No. EP 18157200.9, 9 pgs.
International Search Report and Written Opinion dated May 4, 2018 for Application No. PCT/US2018/017756, 12 pgs.

\* cited by examiner

SURGICAL STAPLER WITH INSERTABLE DISTAL ANVIL TIP

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010, issued as U.S. Pat. No. 8,408,439 on Apr. 2, 2013; and U.S. Pub. No. 2012/0239012, entitled "Motor-Driven Surgical Cutting Instrument with Electric Actuator Directional Control Assembly," published Sep. 20, 2012, issued as U.S. Pat. No. 8,453,914 on Jun. 4, 2013. The disclosure of each of the above-cited U.S. Patents and U.S. Patent Publications is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
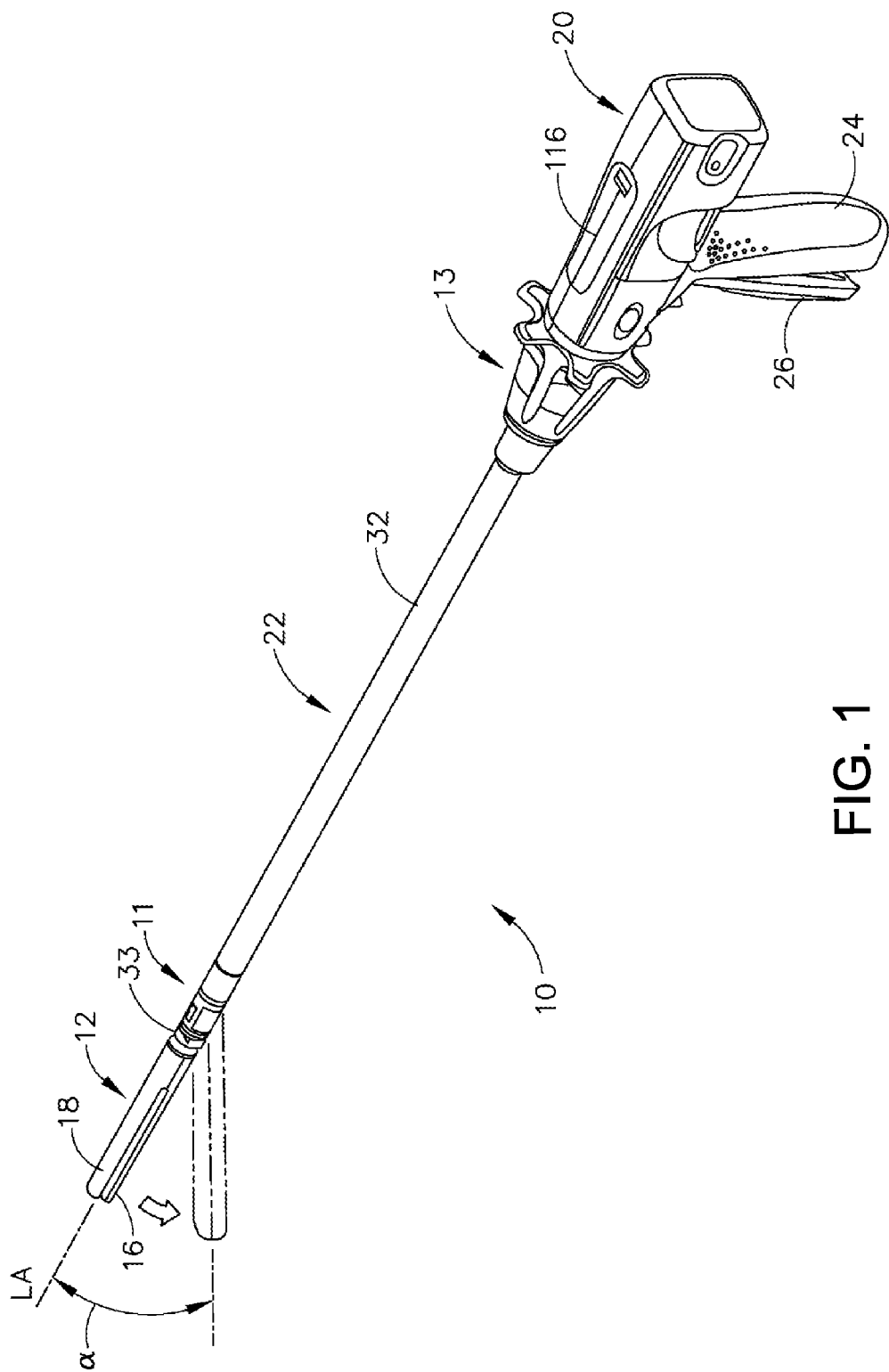
FIG. 1 depicts a perspective view of an exemplary articulating surgical stapling instrument.
Figure 2:
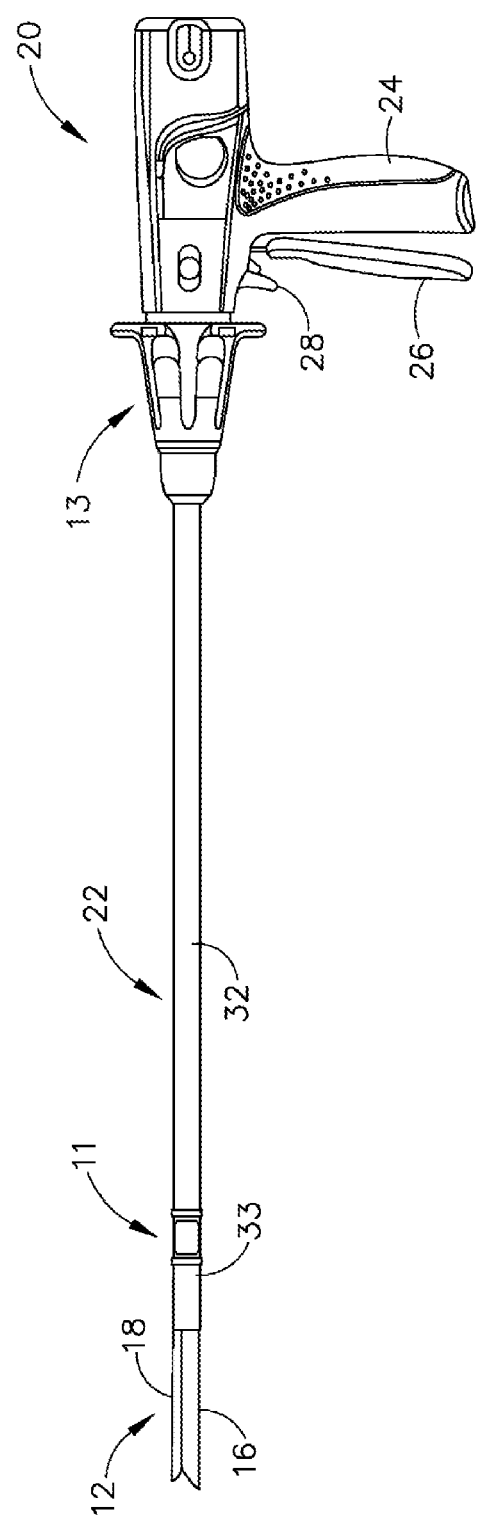
FIG. 2 depicts a side view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-7 depict an exemplary surgical stapling and severing instrument (10) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, instrument (10) may be inserted directly through a thoracotomy or other type of incision. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

In some versions, shaft (22) is constructed in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. By way of further example only, shaft (22) may be detachable from handle portion (20) in accordance with at least some of the teachings of U.S. Pub. No. 2015/0272575, entitled "Surgical Instrument Comprising a Sensor System," published Oct. 1, 2015, issued as U.S. Pat. No. 9,913,642 on Mar. 13, 2018, the disclosure of which is incorporated by reference herein. In some other versions, shaft (22) is not detachable from handle portion (20). Other suitable configurations for shaft (22) will be apparent to those of ordinary skill in the art in view of the teachings herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) may thereby reach behind an organ or approach tissue from a desired angle or for other reasons. In some versions, articulation joint (11) enables deflection of end effector (12) along a single plane. In some other versions, articulation joint (11) enables deflection of end effector along more than one plane. Articulation joint (11) and articulation control (13) may be configured in accordance with the teachings of any of the numerous references that are cited herein. Alternatively, articulation joint (11) and/or articulation control (13) may have any other suitable configuration. By way of example only, articulation control (13) may instead be configured as a knob that rotates about an axis that is perpendicular to the longitudinal axis (LA) of shaft (22).

In some versions, articulation joint (11) and/or articulation control (13) are/is constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein. Articulation joint (11) may also be constructed and operable in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. Other suitable forms that articulation joint (11) and articulation control (13) may take will be apparent to those of ordinary skill in the art in view of the teachings herein.

End effector (12) of the present example includes a lower jaw (16) and a pivotable anvil (18). In some versions, lower jaw (16) is constructed in accordance with at least some of the teachings of U.S. Pub. No. 2014/0239044, entitled "Installation Features for Surgical Instrument End Effector Cartridge," published on Aug. 28, 2014, issued as U.S. Pat. No. 9,808,248 on Nov. 7, 2017, the disclosure of which is incorporated by reference herein. Anvil (18) may be constructed in accordance with at least some of the teachings of U.S. Pub. No. 2014/0239042, entitled "Integrated Tissue Positioning and Jaw Alignment Features for Surgical Stapler," published on Aug. 28, 2014, issued as U.S. Pat. No. 9,517,065 on Dec. 13, 2016, the disclosure of which is incorporated by reference herein; at least some of the teachings of U.S. Pub. No. 2014/0239036, entitled "Jaw Closure Feature for End Effector of Surgical Instrument," published on Aug. 28, 2014, issued as U.S. Pat. No. 9,839,421 on Dec. 12, 2017, the disclosure of which is incorporated by reference herein; and/or at least some of the teachings of U.S. Pub. No. 2014/0239037, entitled "Staple Forming Features for Surgical Stapling Instrument," published on Aug. 28, 2014, issued as U.S. Pat. No. 10,092,292 on Oct. 9, 2018, the disclosure of which is incorporated by reference herein. Other suitable forms that lower jaw (16) and anvil (18) may take will be apparent to those of ordinary skill in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below. Thereafter, triggers (26, 28) may be released to release the tissue from end effector (12).

FIGS. 3-6 depict end effector (12) employing an E-beam form of firing beam (14) to perform a number of functions. It should be understood that an E-beam form is just a merely illustrative example. Firing beam (14) may take any other suitable form, including but not limited to non-E-beam forms. As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing.

Some non-E-beam forms of firing beam (14) may lack upper pin (38), middle pin (46) and/or firing beam cap (44). Some such versions of instrument (10) may simply rely on closure ring (33) or some other feature to pivot anvil (18) to a closed position and hold anvil (18) in the closed position while firing beam (14) advances to the distal position. By way of example only, firing beam (14) and/or associated lockout features may be constructed and operable in accordance with at least some of the teachings of U.S. Pub. No. 2014/0239041, entitled "Lockout Feature for Movable Cutting Member of Surgical Instrument," published on Aug. 28, 2014, issued as U.S. Pat. No. 9,717,497 on Aug. 1, 2017, the disclosure of which is incorporated by reference herein. Other suitable forms that firing beam (14) may take will be apparent to those of ordinary skill in the art in view of the teachings herein.

Figure 3:
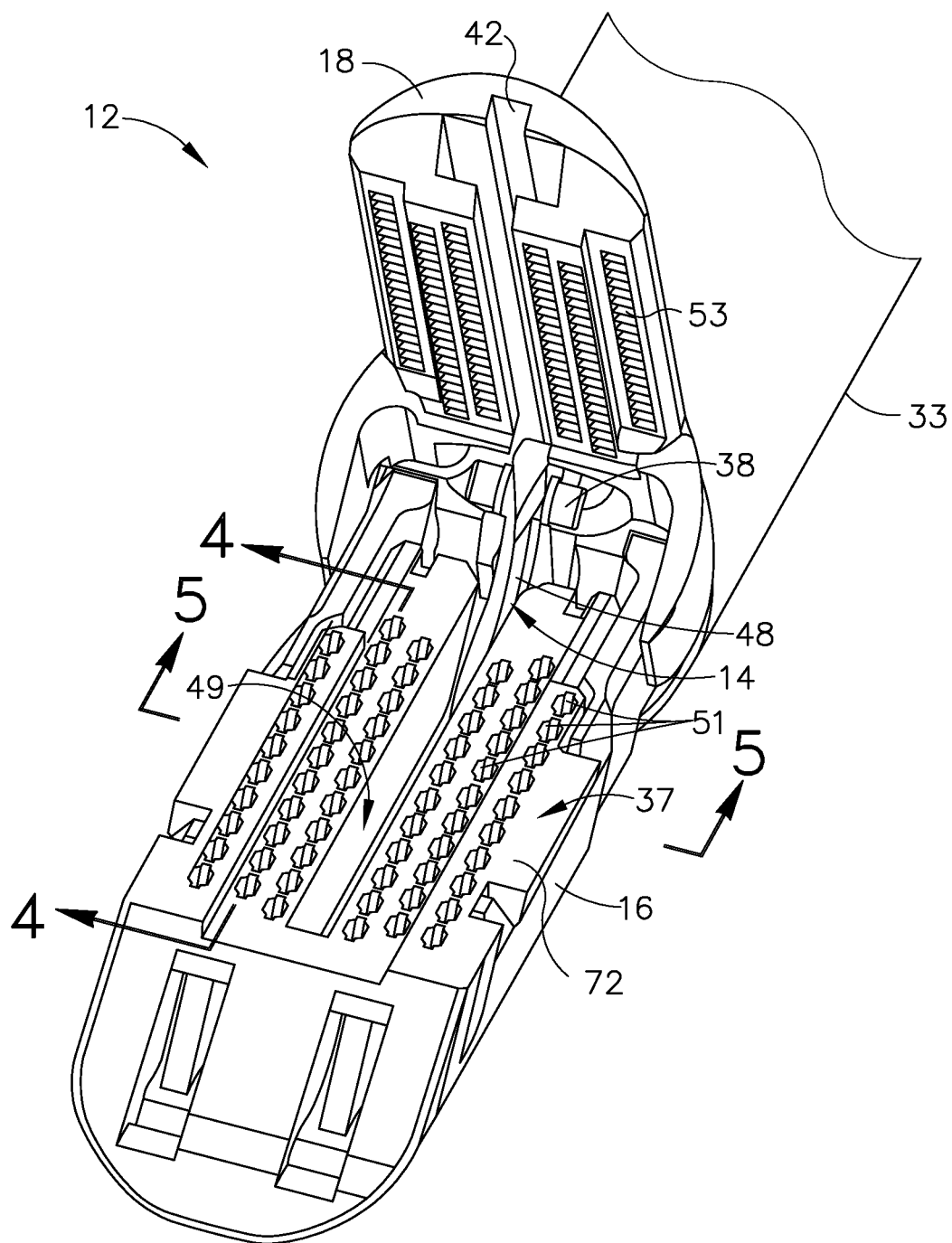
FIG. 3 depicts a perspective view of an opened end effector of the instrument of FIG. 1.
Figure 4A:
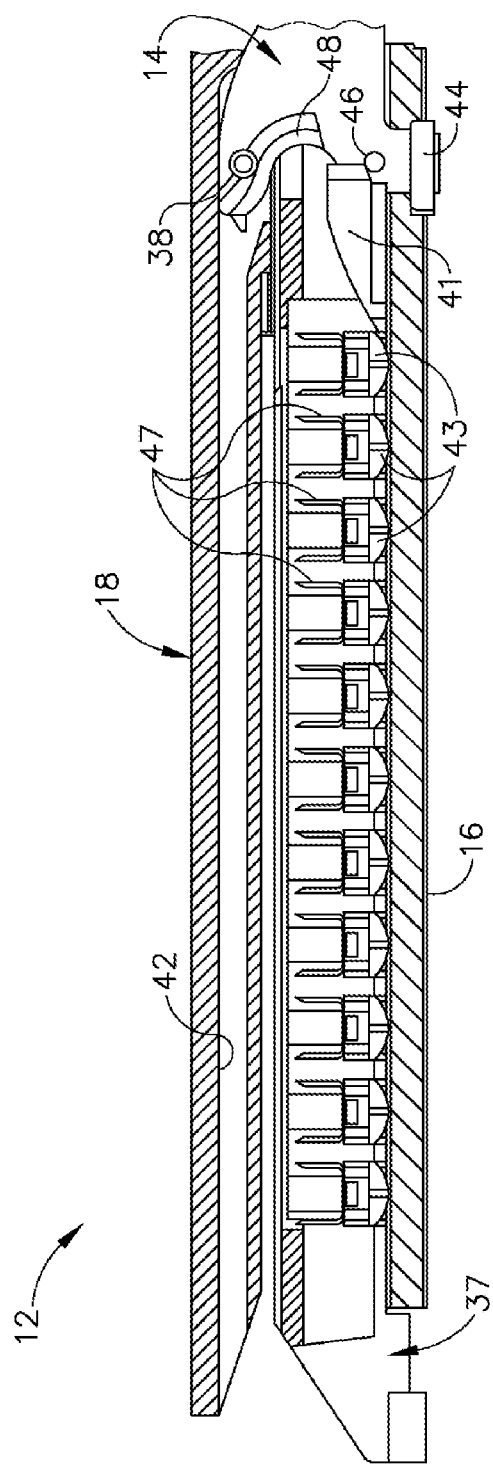
FIG. 4A depicts a side cross-sectional view of the end effector of FIG. 3, taken along line 4-4 of FIG. 3, with the firing beam in a proximal position.
Figure 4B:
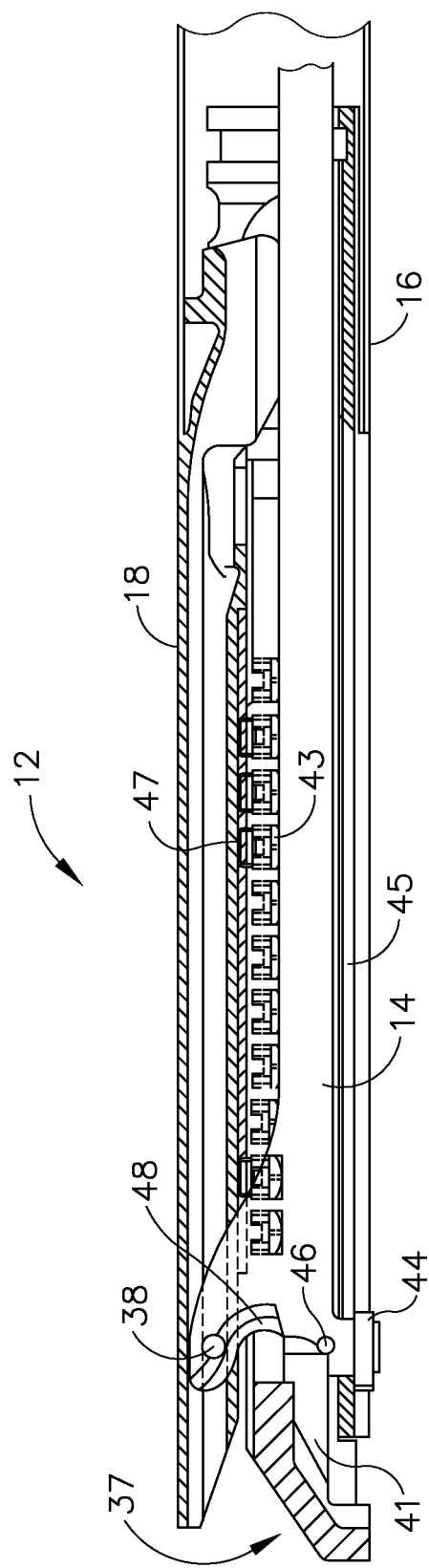
FIG. 4B depicts a side cross-sectional view of the end effector of FIG. 3, taken along line 4-4 of FIG. 3, with the firing beam in a distal position.
Figure 5:
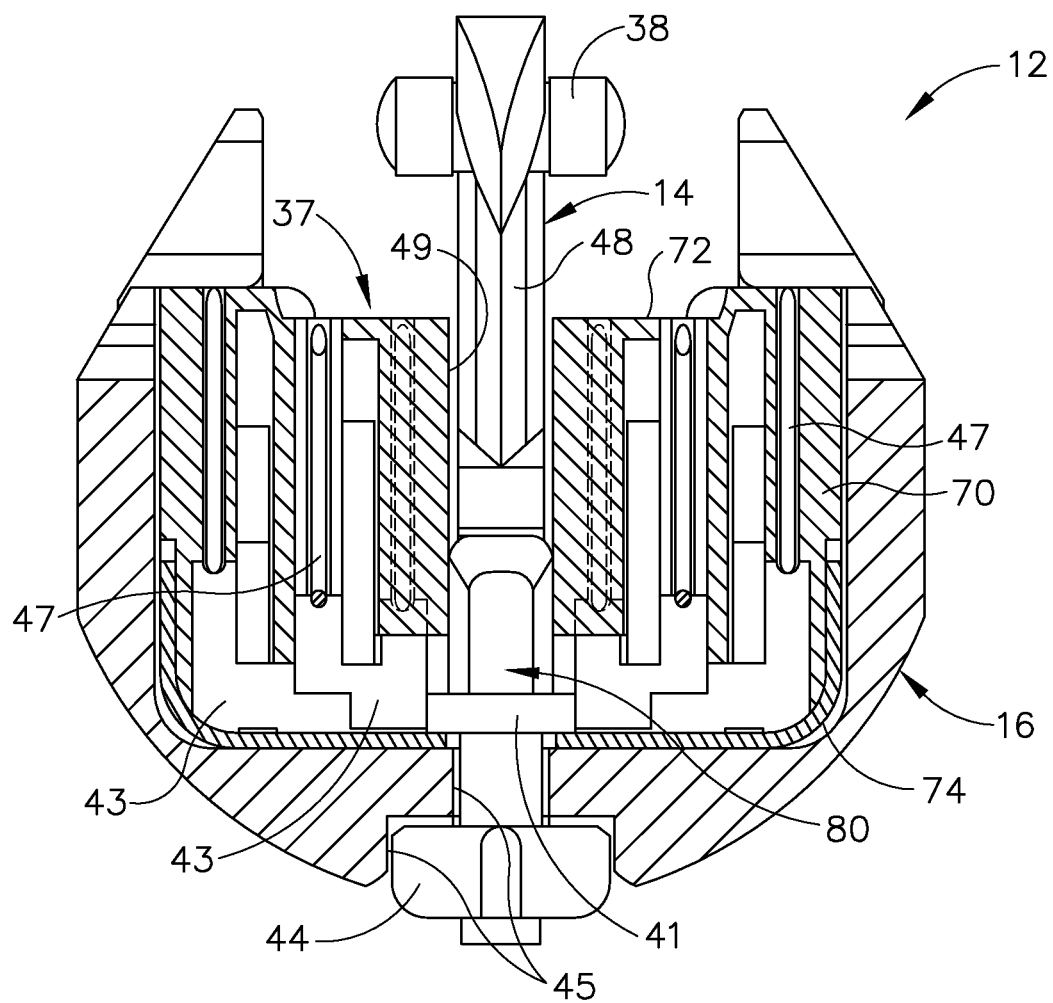
FIG. 5 depicts an end cross-sectional view of the end effector of FIG. 3, taken along line 5-5 of FIG. 3.
Figure 6:
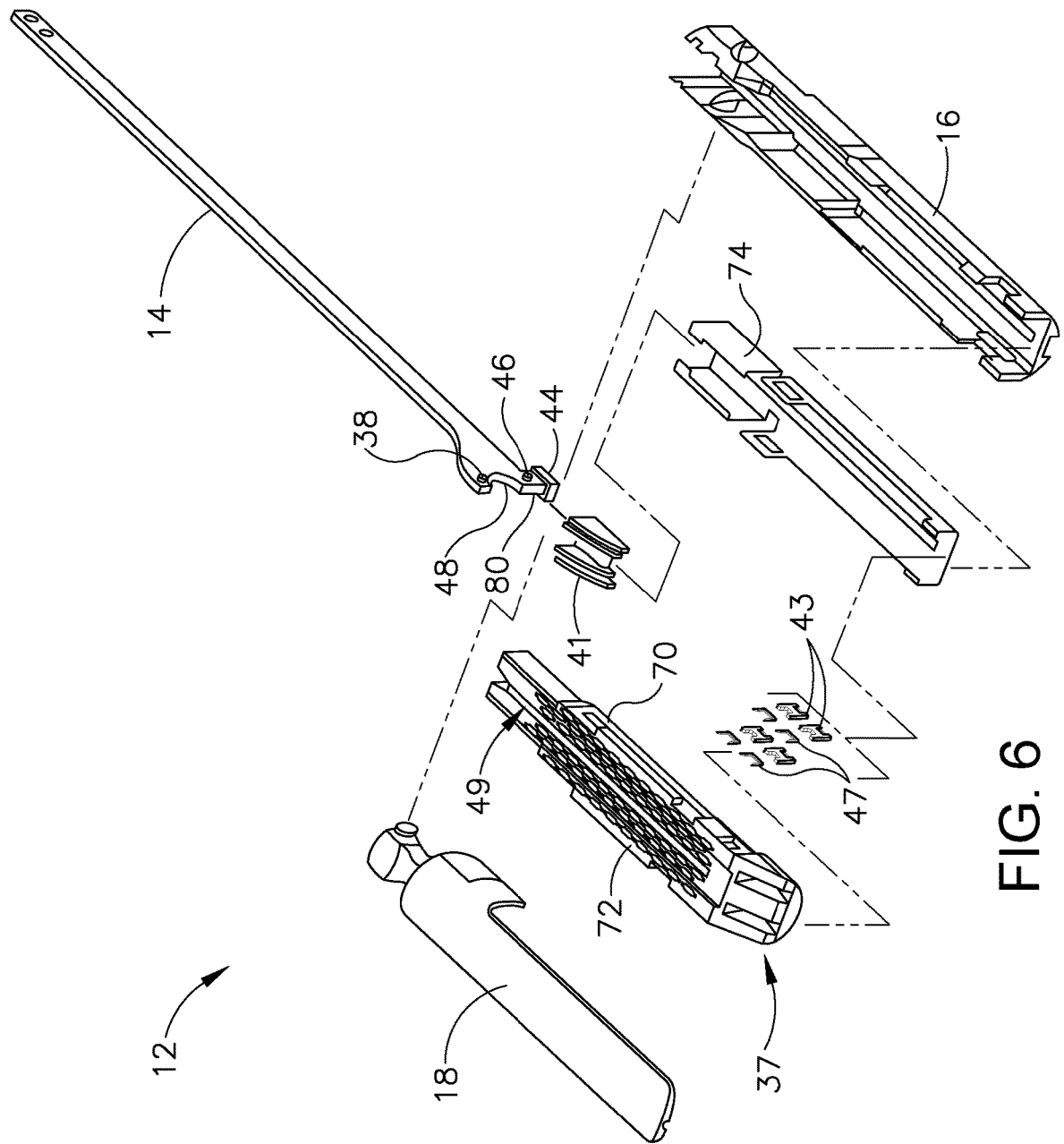
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

In some versions, staple cartridge (37) is constructed and operable in accordance with at least some of the teachings of U.S. Pub. No. 2014/0239042, entitled "Integrated Tissue Positioning and Jaw Alignment Features for Surgical Stapler," published on Aug. 28, 2014, issued as U.S. Pat. 9,517,065 on Dec. 13, 2016, the disclosure of which is incorporated by reference herein. In addition or in the alternative, staple cartridge (37) may be constructed and operable in accordance with at least some of the teachings of U.S. Pub. No. 2014/0239044, entitled "Installation Features for Surgical Instrument End Effector Cartridge," published on Aug. 28, 2014, issued as U.S. Pat. No. 9,808,248 on Nov. 7, 2017, the disclosure of which is incorporated by reference herein. Other suitable forms that staple cartridge (37) may take will be apparent to those of ordinary skill in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14), and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
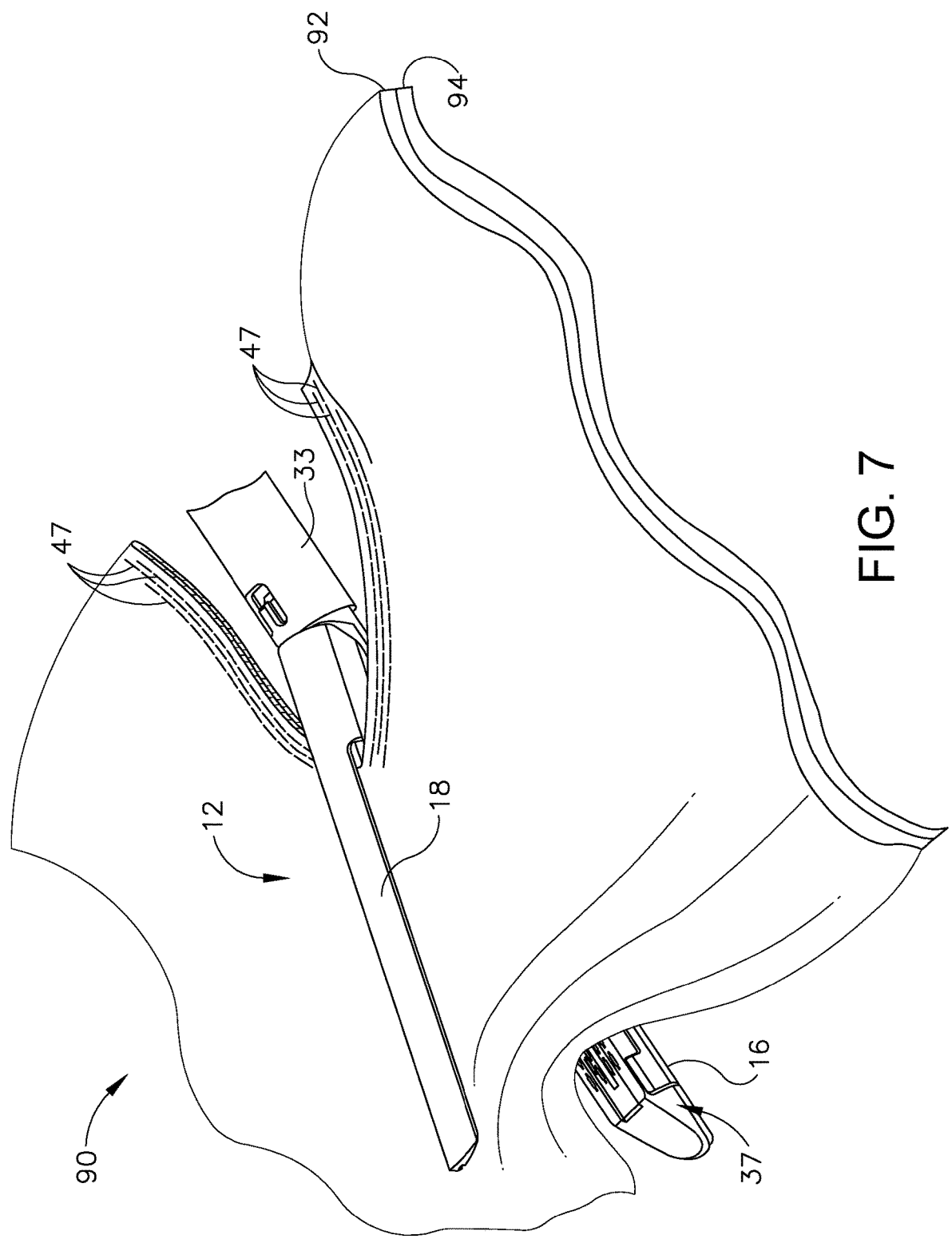
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 7 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Furthermore, while FIG. 7 shows end effector (12) being actuated in two substantially flat, apposed planar layers (92, 94) of tissue, it should be understood that end effector (12) may also be actuated across a tubular structure such as a blood vessel, a section of the gastrointestinal tract, etc. FIG. 7 should therefore not be viewed as demonstrating any limitation on the contemplated uses for end effector (12). Various suitable settings and procedures in which instrument (10) may be used will be apparent to those of ordinary skill in the art in view of the teachings herein.

In one version, instrument (10) provides motorized control of firing beam (14). Exemplary components that may be used to provide motorized control of firing beam (14) are shown and described in US. Pub. No. 2014/0239043, entitled "Distal Tip Features for End Effector of Surgical Instrument," published on Aug. 28, 2014, issued as U.S. Pat. No. 9,622,746 on Apr. 18, 2017, the disclosure of which is incorporated by reference herein. In addition to or in lieu of the foregoing, at least part of the motorized control may be configured in accordance with at least some of the teachings of U.S. Pat. No. 8,210,411, entitled "Motor-Driven Surgical Instrument," issued Jul. 3, 2012, the disclosure of which is incorporated by reference herein. In addition to or in lieu of the foregoing, the features operable to drive firing beam (14) may be configured in accordance with at least some of the teachings of U.S. Pub. No. 2012/0239012, issued as U.S. Pat. No. 8,453,914 on Jun. 4, 2013, the disclosure of which is incorporated by reference herein; and/or in accordance with at least some of the teachings of U.S. Pub. No. 2012/0239012, issued as U.S. Pat. No. 8,453,914 on Jun. 4, 2013, the disclosure of which is also incorporated by reference herein. Other suitable components, features, and configurations for providing motorization of firing beam (14) will be apparent to those of ordinary skill in the art in view of the teachings herein. It should also be understood that some other versions may provide manual driving of firing beam (14), such that a motor may be omitted. By way of example only, firing beam (14) may be actuated in accordance with at least some of the teachings of any other patent/publication reference cited herein.

Instrument (10) may also include a lockout switch and lockout indicator as shown and described in US. Pub. No. 2014/0239043, entitled "Distal Tip Features for End Effector of Surgical Instrument," published on Aug. 28, 2014, issued as U.S. Pat. No. 9,622,746 on Apr. 18, 2017, the disclosure of which is incorporated by reference herein. Additionally, a lockout switch and/or lockout indication and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Instrument (10) also include a manual return switch (116) configured to act as a "bailout" feature, enabling the operator to quickly begin retracting firing beam (14) proximally during a firing stroke. In other words, manual return switch (116) may be manually actuated when firing beam (14) has only been partially advanced distally. Manual return switch (116) may provide further functionality in accordance with at least some of the teachings of U.S. Pub. No. 2014/0239043, entitled "Distal Tip Features for End Effector of Surgical Instrument," published on Aug. 28, 2014, issued as U.S. Pat. No. 9,622,746 on Apr. 18, 2017, the disclosure of which is incorporated by reference herein.

In describing the operation of instrument (10), use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition or in the alternative, the pivot axis may slide along the slot/channel first, with anvil (18) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (18) about an axis that remains fixed and does not translate within a slot or channel, etc.

It should be understood that instrument (10) may be configured and operable in accordance with any of the teachings of U.S. Pat. Nos. 4,805,823; 5,415,334; 5,465,895; 5,597,107; 5,632,432; 5,673,840; 5,704,534; 5,814,055; 6,978,921; 7,000,818; 7,143,923; 7,303,108; 7,367,485; 7,380,695; 7,380,696; 7,404,508; 7,434,715; 7,721,930; U.S. Pub. No. 2010/0264193, issued as U.S. Pat. No. 8,408,439 on Apr. 2, 2013; and/or 2012/0239012, issued as U.S. Pat. No. 8,453,914 on Jun. 4, 2013. As noted above, the disclosures of each of those patents and publications are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary End Effector with Visualization Lead-In, and Gathering Features In some instances, it may be desirable to provide the user with better visualization of end effector (12). In particular, as end effector (12) is inserted into a surgical site, the user may rotate shaft (22) of instrument (10) during the procedure. As a result, end effector (12) also rotates. As end effector (12) rotates, it may be desirable for the user to have visual access to the surgical site. For instance, the user may wish to see the interface or contact between tissue (90) and end effector (12). Since end effector (12) may be rotated about the longitudinal axis (LA) relative to handle portion (20), the user may view the surgical site such that lower jaw (16) of end effector is visible rather than anvil (18). Alternatively, end effector (12) could be rotated such that when the user views end effector (12), anvil (18) is visible by the user. It may be desirable to provide visibility of the surgical site for the user beyond what is possible in instrument (10) of FIG. 1. For instance, in the case of some surgical procedures where fluid carrying vessels are transected and stapled, it may be desirable to have visual confirmation that anvil (18) and lower jaw (16) completely cover the vessel to be cut, such that the vessel may be fully cut and stapled in one single actuation. In other words, the user may wish to avoid cutting and stapling only a portion of a vessel. Thus, some means of visual monitoring and/or feedback may be desirable so that the user will know that end effector (12) has been positioned properly within the surgical site for anvil (18) and lower jaw (16) to fully clamp the vessel. One potential way of monitoring the surgical site may include improving visualization of the area adjacent to the distal tip of lower jaw (16) and anvil (18). Furthermore, not only visualization of the distal end of end effector (12) may be desirable, but also it may be desirable to construct end effector (12) such that the distal end of anvil (18) is configured to urge tissue (e.g., a large vessel) proximally into the space between anvil (18) and lower jaw (16) as anvil (18) closes toward lower jaw (16).

Figure 8:
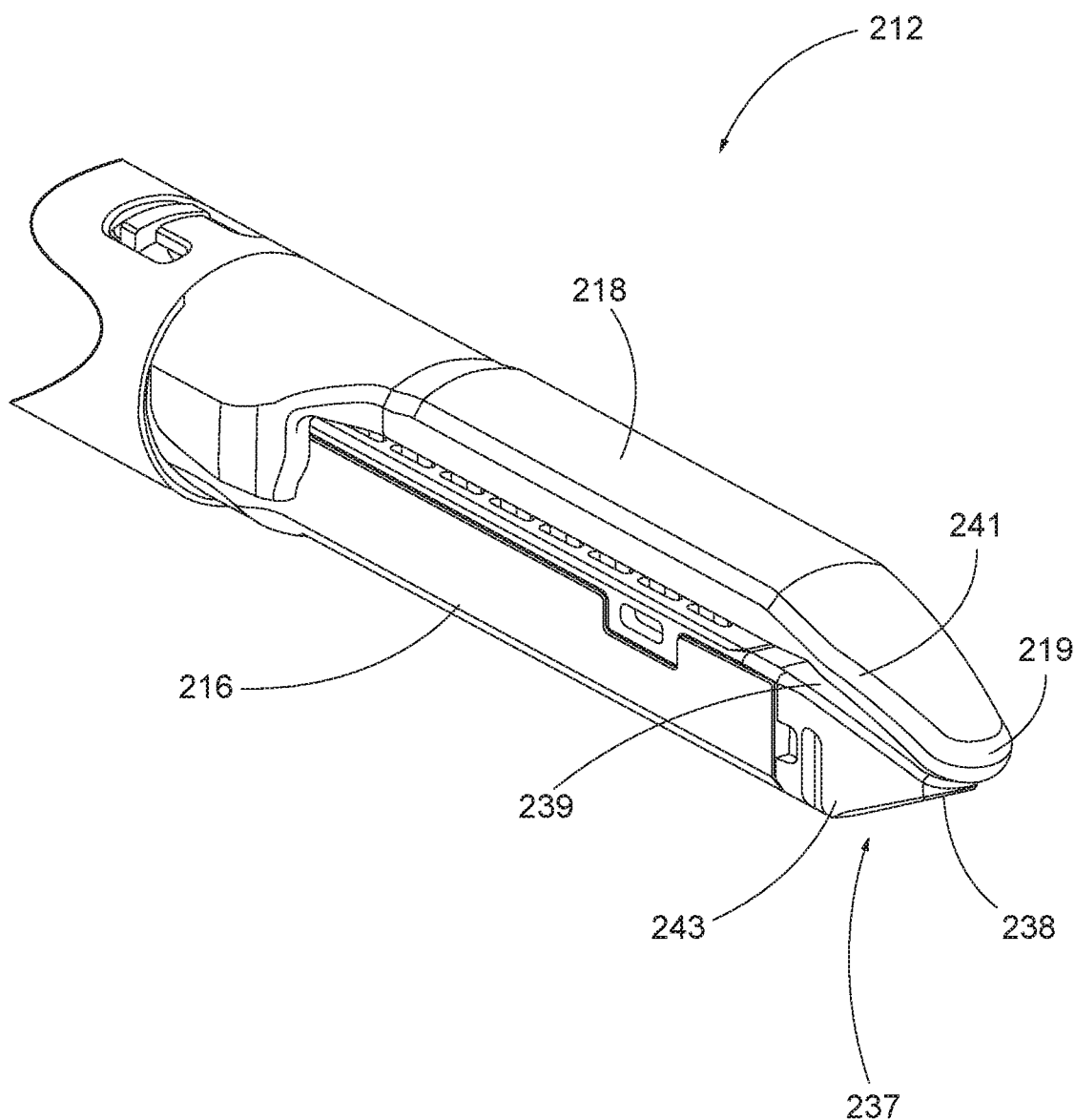
FIG. 8 depicts a perspective view of an alternative version of an end effector with an angled anvil and an angled cartridge.

FIG. 8 depicts an exemplary end effector (212) comprising an anvil (218) and a lower jaw (216). It will be appreciated that end effector (212) may be used in place of end effector (12) of instrument (10). End effector (212) may be integrally formed with instrument (10) or in the alternative may be interchangeable with end effector (12) of instrument (10).

Anvil (218) is operable to pivot relative to lower jaw (216). Anvil (218) and lower jaw (216) may clamp tissue (90) similarly to clamping performed by anvil (18) and lower jaw (16) shown in FIG. 1. End effector (212) further comprises a cartridge (237) operable to be placed in lower jaw (216) similarly to cartridge (37) shown in FIG. 3.

Figure 9:
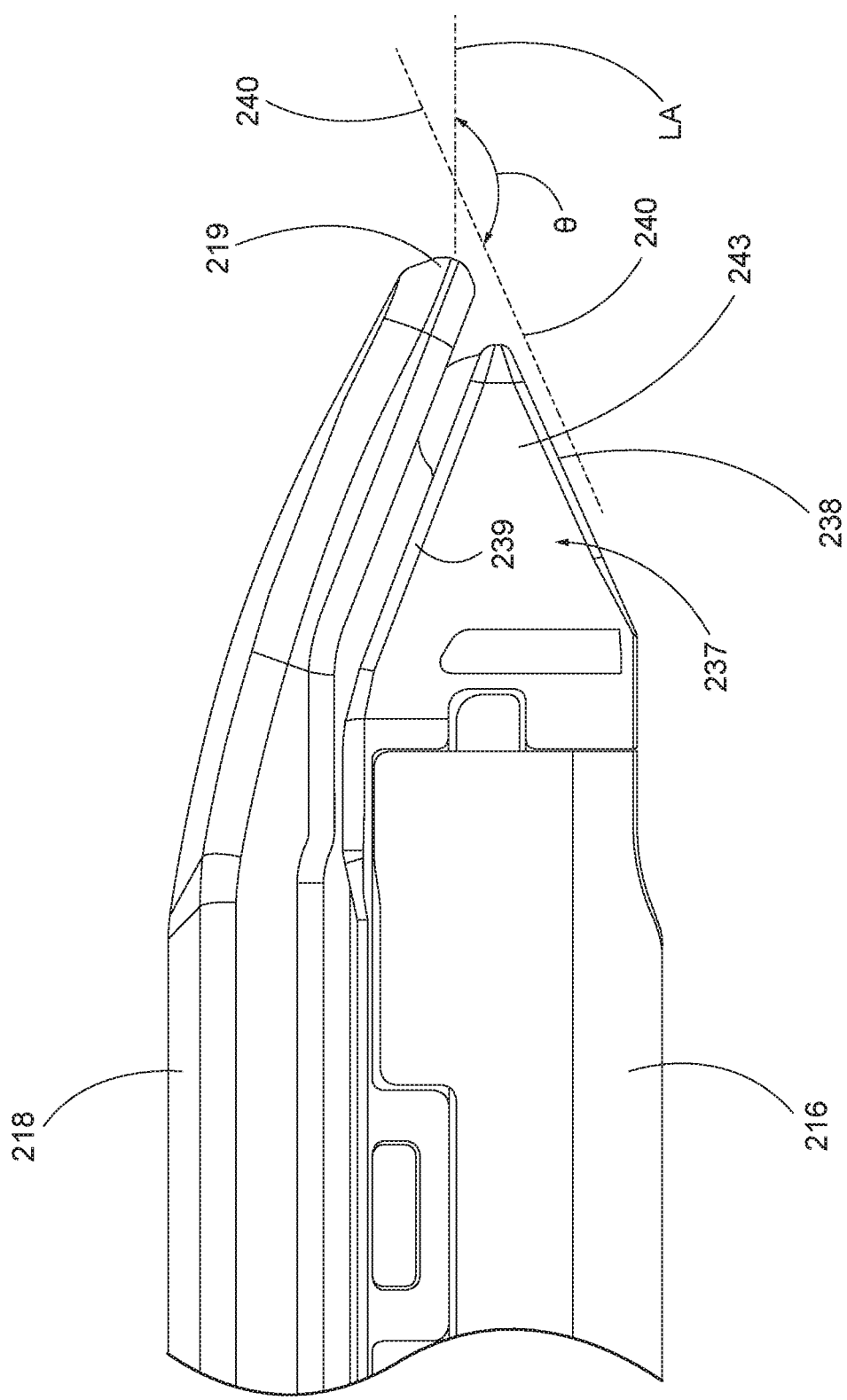
FIG. 9 depicts an enlarged, side view of the end effector of FIG. 8.
Figure 10:
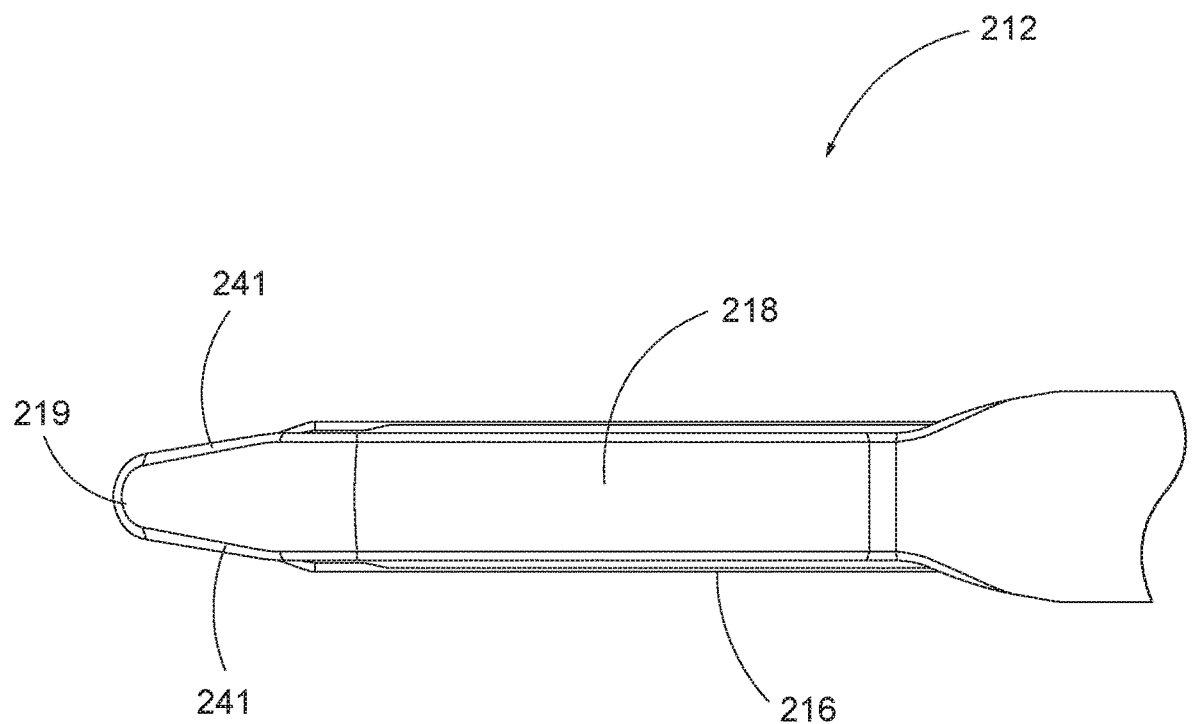
FIG. 10 depicts an enlarged top view of the end effector of FIG. 8.

Anvil (218) as can be seen in FIGS. 8-10 has an elongated shape where the distal portion of anvil (218) angles toward cartridge (237). The distal portion of anvil (218) angles toward cartridge (237) such that the distal most tip (219) of anvil (218) extends distally longitudinally further than cartridge (237). Though in some versions, distal tip (219) may extend to a distance longitudinally equal to cartridge (237) or proximal relative to the distal most point on cartridge (237). Furthermore, anvil (218) angles toward cartridge (237) through a gentle slope. As seen best in FIG. 10, anvil (218) includes sides (241) that taper as they approach the distal most tip (219) of anvil (218). By way of example, anvil (218) is shaped in FIG. 8 similarly to an inverted ski tip. The angled shape of anvil (218) may provide easier insertion of end effector (212) into a surgical site. For instance, the gentle slope or inverted ski tip shape of anvil (218) may provide an atraumatic tissue deflection surface as anvil (218) contacts or moves through tissue. Such atraumatic tissue deflection may include urging tissue (e.g., a large vessel) proximally into the space between anvil (218) and lower jaw (216) as anvil (218) closes toward lower jaw (216). Once placed into a surgical site, the angled shape of anvil (218) may also provide better maneuverability of end effector (212) and better visibility of the distal end of end effector (212) in relation to anatomical structures at the surgical site. Other suitable variations of anvil (218) will be apparent to one of ordinary skill in the art in view of the teachings herein.

Cartridge (237) is operable to hold staples similar to staples (47) shown in FIG. 4A for driving into tissue. As shown in FIG. 9, the distal end of cartridge (237) has a triangular profile. In particular, the distal end of cartridge (237) comprises an upper tapered surface (239) and a lower tapered surface (238). Additionally, the distal end of cartridge (237) comprises a tapered side surface (243) on each side. In the present example, each tapered side surface (243) of cartridge (237) generally aligns with the taper presented by sides (241) of anvil (218). Thus, as shown in FIG. 10, side surfaces (243) of cartridge (237) do not extend outwardly from longitudinal axis (LA) of end effector (212) past sides (241) of anvil (218). Upper tapered surface (239) and lower tapered surface (238) lead to the distal most end of cartridge (237). Lower tapered surface (238) defines a sight line (240) such that once end effector (212) is inserted into a surgical site, the user can see along sight line (240). Sight line (240) extends along the edge of lower tapered surface (238). It will be appreciated that the planar shape of lower tapered surface (238) may be operable to allow the user to visualize and/or nearly visualize the distal tip (219) of anvil (218). In particular, sight line (240) intersects longitudinal axis (LA), which extends longitudinally through end effector (212), to form a viewing angle (θ).

Viewing angle (θ) may establish the relative visibility that a user has regarding distal tip (219). In particular, the user can see in front of distal tip (219) along any line of sight that passes through the intersection of sight line (240) and longitudinal axis (LA) within viewing angle (θ). For instance, as viewing angle (θ) increases, the user would have greater visibility of the area immediately in front of distal tip (219) from proximal vantage points; whereas as viewing angle (θ) decreases, the user has less visibility of the area in front of distal tip (219) from proximal vantage points. In some versions, viewing angle (θ) defines an angle greater than 90 degrees. Additionally, in some versions, viewing angle (θ) defines an angle greater than 135 degrees. Other suitable angles for viewing angle (θ) will be apparent to one of ordinary skill in the art in view of the teachings herein. In the illustrated version, the user generally looks along sight line (240) or along some other line of sight within viewing angle (θ), thus, the user has visibility along sight line as well as any area within viewing angle (θ). The underside of distal tip (219) is further slightly rounded to aid in the visibility of the intersection of longitudinal axis (LA) and sight line (240).

When tissue (90) is clamped between a closed cartridge (237) and anvil (218), the user can look along sight line (240) or elsewhere within viewing angle (θ) to see, for instance, precisely where anvil (218) has clamped tissue (90). Furthermore, the user would be able to determine whether the tissue is completely clamped between anvil (218) and cartridge (237) such that tissue does not spill over the end of end effector (212). The user may be able to also visualize the quality of the clamp between anvil (218) and cartridge (237) against tissue (90). It will be appreciated that in some instances, end effector (212) may be rotated before, during, or after clamping tissue (90). As a result, the tapered shape of anvil (218) may also provide more accessible viewing of distal tip (219) or substantially adjacent distal tip (219). The taper of anvil (218) along with lower tapered surface (238) of cartridge (237) may further promote easy insertion of end effector (212) into tissue in an atraumatic manner. Furthermore, it may be easier to fit end effector (212) through a trocar or other devices operable to introduce end effector (212) into a surgical site due to the tapered end of end effector (212). For instance, once distal tip (219) is fit into a trocar, lower tapered surface (238) and the tapered shape of anvil (218) may provide a lead-in, guiding the rest of end effector (212) into the trocar. In view of the teachings herein, those of ordinary skill in the art will further appreciate that visibility and maneuverability can be enhanced by the tapered design for both sides (241) of anvil (218) and each side (243) of cartridge (237).

In addition to the foregoing, end effector (212) and versions of instrument (10) incorporating end effector (212) may be configured and operable in accordance with at least some of the teachings of U.S. Pat. No. 9,186,142, entitled "Surgical Instrument End Effector Articulation Drive with Pinion and Opposing Racks," issued Nov. 17, 2015, the disclosure of which is incorporated by reference herein; U.S. Pub. No. 2014/0239041, entitled "Lockout Feature for Movable Cutting Member of Surgical Instrument," published Aug. 28, 2014, issued as U.S. Pat. No. 9,717,497 on Aug. 1, 2017, the disclosure of which is incorporated by reference herein; U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017, the disclosure of which is incorporated by reference herein; U.S. Pub. No. 2014/0239043, entitled "Distal Tip Features for End Effector of Surgical Instrument," published Aug. 28, 2014, issued as U.S. Pat. No. 9,622,746 on Apr. 18, 2017, the disclosure of which is incorporated by reference herein; U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein; U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein; and/or U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Further modifications that may be incorporated into end effector (212) will be described in greater detail below.

III. Modular Curved Anvil Tips for End Effectors

In some procedures, it may be necessary to cut along tissue or through tissue where more than one cutting sequence is necessary to complete the procedure—in other words making sequential cuts along a continuous path. In such procedures, this sequential cutting technique can be defined as "marching." With procedures that involve marching, instrument (10) may be placed at the surgical site, actuated to cut and staple, then removed from the surgical site for installing a new cartridge (37), and then be placed back at the surgical site again for the next cut and staple along the same path in which the previous cutting and stapling cycle occurred. This process is repeated until the cut and staple procedure is complete. As can be seen in FIGS. 4A-4B and FIG. 7, the distal end configuration of end effector (12) provides a gap between the distal end of anvil (18) and the distal end of cartridge (37). This gap may facilitate marching by providing an atraumatic space for tissue to enter the distal end of end effector (12) at the beginning of each marching step.

As noted above, the distal end configuration of end effector (212) is different from the distal end configuration of end effector (12); with the different configuration of end effector (212) providing different potential advantages. In particular, the distal end configuration of end effector (212) may provide improved maneuverability and improved visibility of the relationship between the distal end of end effector (212) and adjacent anatomical structures. In addition, the distal end configuration of end effector (212) may provide tissue-gathering effects by urging tissue proximally into the space between anvil (218) and lower jaw (216) as anvil (218) is closed toward lower jaw (216). However, in versions where all the structures of end effector (212) are rigid, the bent configuration of distal tip (219) of anvil (218) may not lend itself well to marching operations, as distal tip (219) may impart trauma to tissue that is not gathered into the space between anvil (218) and lower jaw (216) as anvil (218) is closed toward lower jaw (216). Thus, in versions where all the structures of end effector (212) are rigid, end effector (212) may be best suited for cutting and stapling operations (e.g., vessel transection) where all of the tissue that is to be cut and stapled is gathered proximal to distal tip (219).

In view of the foregoing, it may be desirable to provide a variation of end effectors (12, 212) that provides the marching capabilities of end effector (12), the improved visibility associated with end effector (212), and the tissue gathering capabilities of end effector (212), without providing an increased risk of trauma that might otherwise be associated with fully rigid versions of end effector (212). The following describes several merely illustrative examples of such variations of end effectors (12, 212). In the following examples, an anvil has a distal tip that is resiliently biased to assume a bent or angled configuration like distal tip (219); yet the resiliently biased distal tip is deflectable away from the lower jaw in response to a sufficient load on the distal tip. It will be understood in view of the teachings herein that providing an anvil with an elastically deformable angled distal tip portion can provide an additional level of maneuverability benefits in terms of navigating through tissue to a surgical site. In this manner, the deformable distal tip portion may deflect or deform to promote smooth and atraumatic movement of the end effector through tissue, particularly during marching operations. Additionally, with an anvil having a bias to an angled position when not in a loaded state or contacted by surrounding tissue, enhanced visualization during tissue capture and cutting can be achieved compared to using end effectors with a straight or non-angled anvil. Moreover, an anvil with a distal tip that is biased to an angled position may provide some degree of tissue gathering effects up until reaching a load point that would be associated with marching rather than being associated with simply gathering a relatively small tissue structure between the anvil and lower jaw.

A. Tip with Resilient Plug

Figure 11:
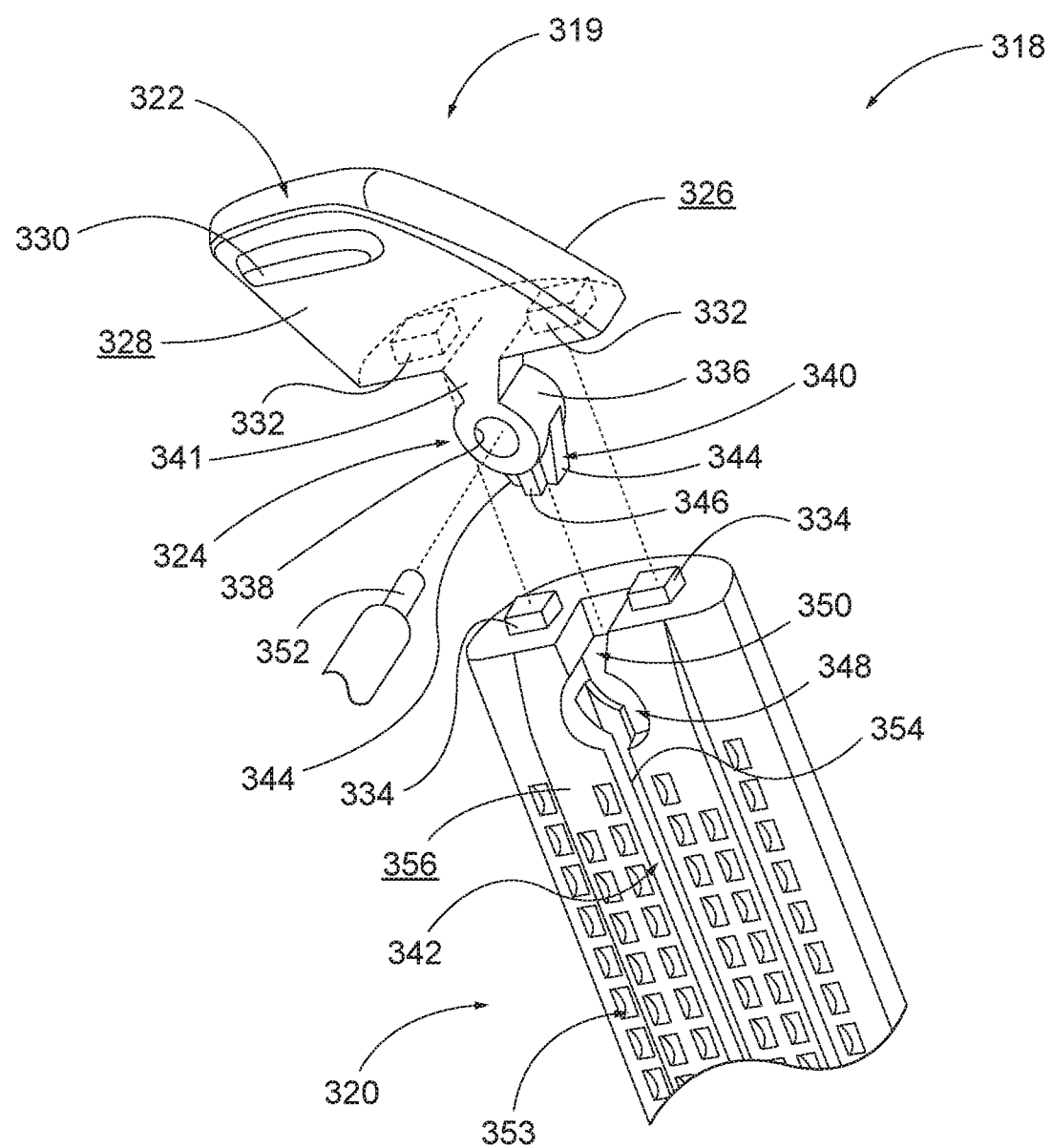
FIG. 11 depicts an enlarged exploded perspective view of a distal portion of an alternative version of an anvil of an end effector, with the anvil having a curved modular tip.

FIG. 11 shows an exemplary anvil (318) suitable for use with any of the end effectors and surgical instruments described herein. Anvil (318) comprises a tip (319) and a body (320). Tip (319) is selectively connectable with body (320) such that tip (319) is configured as a modular and releasable tip. In the illustrated version of FIGS. 11-14, tip (319) is curved such that tip (319) extends distally from body (320) in a curved fashion where tip (319) curves or bends away from a longitudinal axis defined by body (320) downward or in the direction toward a staple cartridge of the end effector as shown and described above and that is usable with anvil (318). While shown as curved in the illustrated version, in some other versions, tip (319) can be straight such that it extends along the longitudinal axis defined by body (320). As used herein, the terms "angled" and "curved" shall be read as being synonymous with each other when referring to a distal end configuration of a component of an end effector. In other words, the term "curved" (and variations thereof) may include a relationship between two straight features that together define an angle, such that the term "curved" (and variations thereof) should not be read as requiring a component to necessarily extend along an arc.

Tip (319) comprises distal end (322) and proximal end (324). Distal end (322) is configured as an exterior portion of tip (319) that remains outside of body (320) when tip (319) is connected with body (320). Proximal end (324) is configured as an interior portion of tip (319) that is positioned within body (320) when tip (319) is connected with body (320). Distal end (322) of tip (319) further comprises a top surface (326) and a bottom surface (328). Bottom surface (328) is operably configured as a contacting surface that contacts tissue when the end effector clamps tissue.

Tip (319) further comprises ridge (330) on bottom surface (328). Ridge (330) is operably configured as a tissue gripping feature to assist with gripping tissue when the end effector is in a closed position clamping tissue. In the present example, ridge (330) is located close to the distal-most part of distal end (322), and ridge (330) extends transversely across distal end (322) such that ridge (330) generally extends in a direction perpendicular to the longitudinal axis defined by body (320) of anvil (318).

Tip (319) further comprises one or more recesses (332). In the illustrated version, tip (319) has two recesses (332), although in other versions tip (319) can have greater or fewer recesses (332). Recesses (332) are located in distal end (322) and are positioned such that they align with corresponding protrusions (334) on body (320). In this manner, protrusions (334) are positionable within recesses (332) to align tip (319) with body (320) when connecting tip (319) to body (320). Thus, in the present example, recesses (332) and protrusions (334) are operably configured as alignment features.

At proximal end (324) of tip (319) is a plug (336). Plug (336) comprises a cut-out (338) within its center, and a guide feature (340) at its proximal-most end. A neck portion (341) of tip (319) connects plug (336) with distal end (322). In the present example, plug (336) is constructed of a resilient material, e.g. an elastomeric material. As will be described further below, the resiliency of plug (336) provides plug (336) with the ability to deform when a sufficient force is applied to plug (336), and then to return to its initial configuration when the force is removed. As best seen in FIG. 11, guide feature (340) comprises two lateral portions (344) separated by a center portion (346).

Body (320) of anvil (318) comprises protrusions (334) that are configured to fit within recesses (332) of tip (319) as mentioned above. Body (320) further comprises a plurality of staple forming pockets (353) that are similar in structure and function to staple forming pockets (53) described above. Body (320) further comprises longitudinal anvil slot (342). Along a proximal portion of body (320), longitudinal anvil slot (342) has a T-shape portion (354) similar to longitudinal anvil slot (42) as seen in FIG. 3. Near the distal end of body (320), however, longitudinal anvil slot (342) comprises a cylindrical shaped portion (348) configured to receive cylindrical shaped plug (336). Further nearer the distal end of body (320), longitudinal anvil slot (342) comprises a V-shape portion (350) configured to receive V-shaped neck portion (341).

Figure 12:
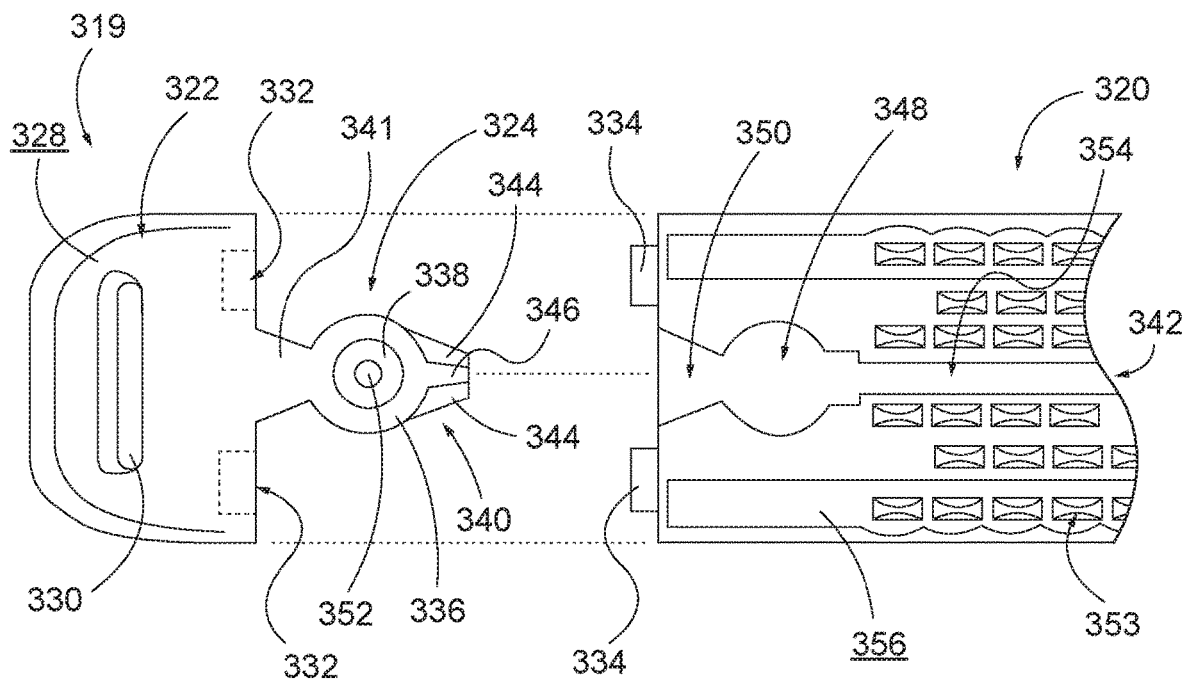
FIG. 12 depicts an enlarged bottom view of the distal portion of the anvil of FIG. 11, shown with the modular tip separated from the body of the anvil.
Figure 13:
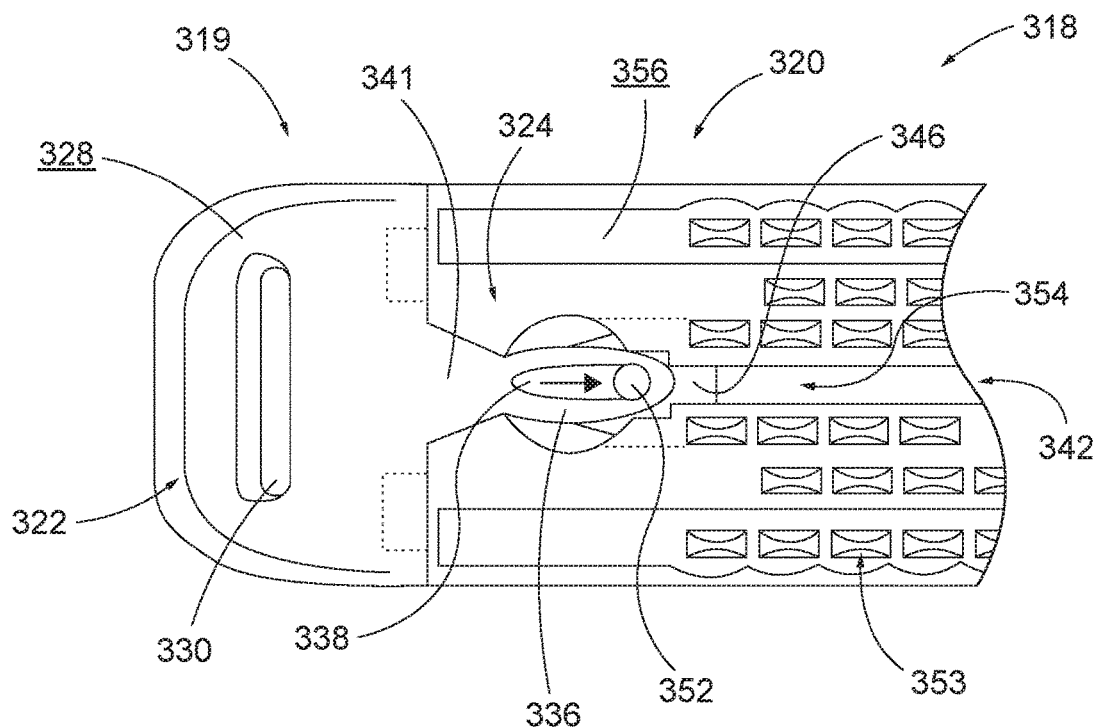
FIG. 13 depicts an enlarged bottom view of the distal portion of the anvil of FIG. 11, shown with the modular tip in a first state when inserted within the body of the anvil.
Figure 14:
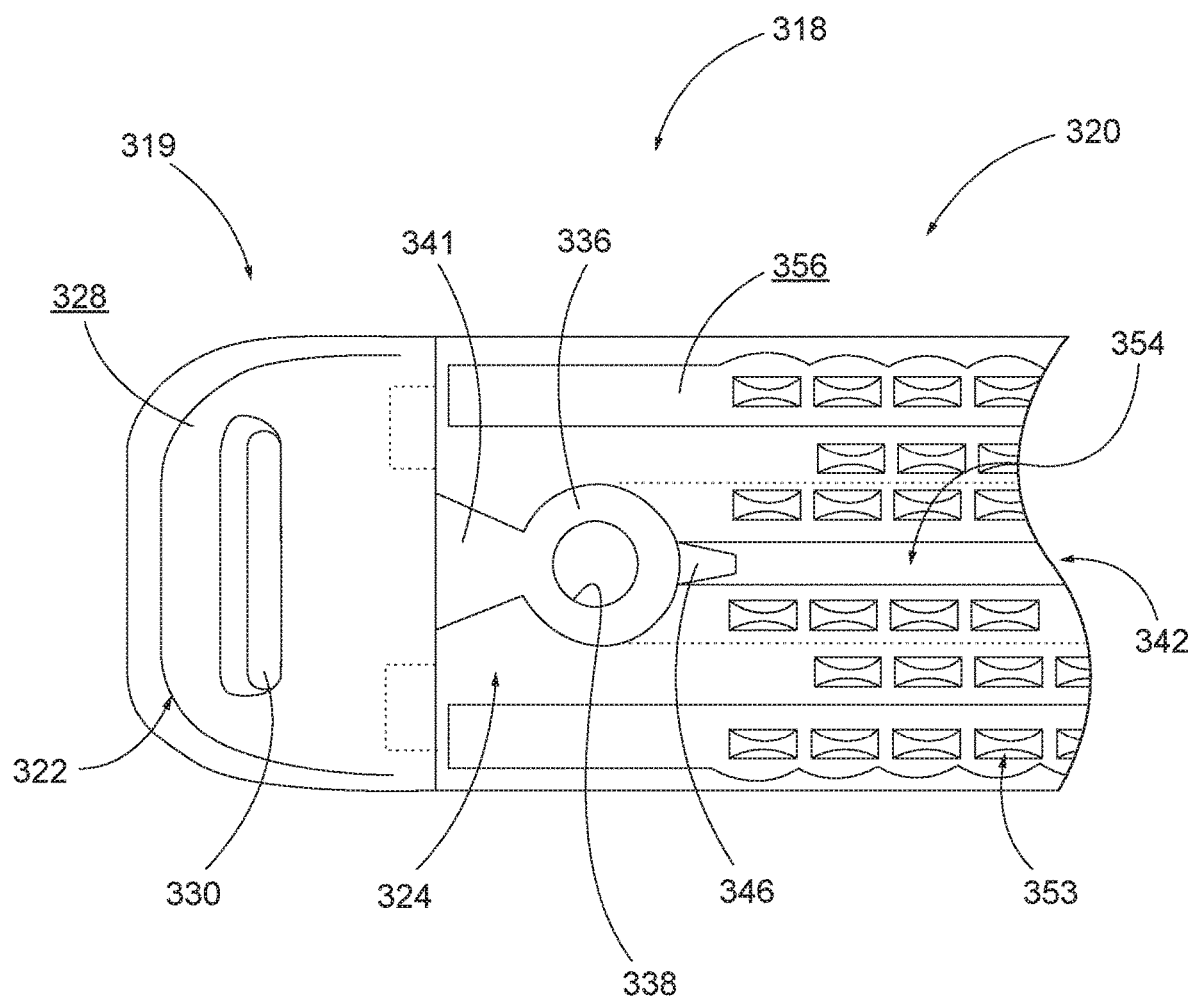
FIG. 14 depicts an enlarged bottom view of the distal portion of the anvil of FIG. 11, shown with the modular tip in a second state when inserted within the body of the anvil.

FIGS. 12-14 depict a sequence of views showing tip (319) being connected with body (320). Beginning with FIG. 12, tip (319) and body (320) are positioned spaced apart but in general alignment with one another. A tool having a post (352) is used by inserting post (352) within cut-out (338) of plug (336). The tool with post (352) then advanced toward body (320) such that it pulls tip (319) toward body (320). As tip (319) is advanced or moved toward body (320), guide feature (340) slides within longitudinal anvil slot (342). In this manner, guide feature (340) first enters V-shaped portion (350) of longitudinal anvil slot (342), and with continued pulling of tip (319) in a proximal direction, guide feature (340) passes V-shaped portion (350) and enters cylindrical shaped portion (348).

With guide feature (340) past V-shaped portion (350), plug (336) now enters body (320) at V-shaped portion (350) of longitudinal anvil slot (342). Plug (336) is configured with a cylindrical shape in the present example. V-shaped portion (350) of longitudinal anvil slot (342) narrows as it extends proximally. Plug (336) has a size that initially fits within the wide end of V-shaped portion (350). However, further proximally along V-shaped portion (350), plug (336) is sized such that its diameter is greater than the width of V-shaped portion (350). As mentioned above, plug (336) is resilient and with continued force applied to plug (336) in a proximal direction, plug (336) deforms by stretching and narrowing as shown in FIG. 13. This deformation of plug (336) enables plug (336) to pass through V-shaped portion (350) and enter cylindrical shaped portion (348) of longitudinal anvil slot (342). Stated another way, plug (336) elongates to ultimately slide through V-shaped portion (350) and into cylindrical portion (348). Furthermore, when this occurs, guide feature (340) continues to move proximally, passing cylindrical shaped portion (348) and entering T-shaped portion (354) of longitudinal anvil slot (342).

Referring to FIG. 14, once plug (336) is located within cylindrical portion (348) of longitudinal anvil slot (342) of body (320), post (352) of the tool can be removed from center cut-out (338) of plug (336). This removal of post (352) removes the proximal force previously being applied to plug (336) to elongate plug (336). With the force removed, plug (336) returns to its initial, non-deformed, state, where plug (336) is no longer elongated and thus returns to its cylindrical shape such that plug (336) fits securely within cylindrical portion (348) of longitudinal anvil slot (342). In some examples, before post (352) is removed from cut-out (338), the proximal force is removed from the tool such that plug (336) returns to its initial, or at-rest or relaxed, state before post (352) is removed from cut-out (338) of plug (336).

With tip (319) inserted within, or connected with, body (320), as shown in FIG. 14, protrusions (334) fit within recesses (332), guide feature (340) fits within T-shaped portion (354) of longitudinal anvil slot (342), plug (336) fits within cylindrical portion (348) of longitudinal anvil slot (342), and neck portion (341) fits within V-shaped portion (350) of longitudinal anvil slot (342). Moreover, lateral portions (344) of guide feature (340) fit within horizontal or laterally extending portions of T-shaped portion (354) of slot (342). Additionally, center portion (346) of guide feature (340) fits within a vertically extending portion of T-shaped portion (354) such that center portion (346) fits within slot (342) closest to a bottom surface (356) of body (320). In the present example, guide feature (340) is configured such that its most proximal location within T-shaped portion (354) remains distal to the distal-most travel of firing beam (14) as described above.

With the configuration described above, tip (319) and body (320) comprise a plurality of retaining features that are operably configured to selectively secure tip (319) with body (320). In this manner, the retaining features comprise one or more of the complementary interfaces described above. For instance the fit of one of protrusions (334) within one of recesses (332) would represent a complementary interface and thus one of the plurality of retaining features. Similarly, the fit of plug (336) within cylindrical portion (348) of slot (342) would be another. While in the present example there are multiple retaining features configured to secure tip (319), in other versions the precise number of retaining features can be greater or fewer. In some variations, a rigid pin (not shown) or other retaining member is inserted into cut-out (338) after tip (319) is fully seated in body (320) as shown in FIG. 14. Such a pin or other retaining member may prevent plug (336) from inadvertently collapsing during use of anvil (318), thereby preventing inadvertent decoupling of tip (319) from body (320) during use of anvil (318). Also, the precise shapes and configurations for plug (336), protrusions (334), recesses (332), neck portion (341), cut-out (338), guide feature (340), and slot (342) are merely exemplary. In view of the teachings herein, other shapes for and modifications to these features will be apparent to those of ordinary skill in the art.

Tip (319) is also removable from body (320) such that tip (319) may be replaced due to wear and tear, or for a different tip configuration, or for any other reason. To remove tip (319), post (352) is inserted within cut-out (338). With post (352) within cut-out (338), a user may grasp distal end (322) of tip (319) and pull tip (319) distally away from body (320). At the same time, post (352) may be held stationary such that the resilient nature of plug (336) promotes elongation and narrowing of plug (336) in response to the distal pulling force being applied to tip (319). This allows for plug (336) to narrow at its distal-most end such that it can fit within and pass from cylindrical portion (348) to V-shaped portion (350) of slot (342). In a similar fashion, guide feature (340) is also resilient such that it elongates similar to plug (336), which enables guide feature (340) to pass through cylindrical portion (348) to V-shaped portion (350) as well.

In some other examples of removal of tip (319), post (352) may be omitted from use. In such an example, a sufficient distal force applied to tip (319) causes plug (336) to contact the interior sidewalls of body (320) at the intersection of cylindrical portion (348) and V-shaped portion (350) of slot (342). The force applied will transfer to plug (336) and cause plug (336) to deform by elongating or narrowing such that plug (336) is able to pass from cylindrical portion (348) to V-shaped portion (350). The same deformation and elongation will occur with guide feature (340) as described above. This in turn will allow for removal of tip (319) without the need to use the tool with post (352). In view of the teachings herein, other ways to remove tip (319) will be apparent to those of ordinary skill in the art.

In the present example, tip (319) is elastically deformable such that in use, during clamping tissue for example, tip (319) may deflect or bend from a curved state to a straight or less curved state. By way of example only, tip (319) may be deflectable between about 20 degrees and about 70 degrees in a downward direction from a longitudinal axis toward cartridge; between about 0 degrees and about 90 degrees in an upward direction from a longitudinal axis toward cartridge (37). The degree of deflection may be influenced by the thickness and/or density of the tissue that is being compressed between anvil (318) and cartridge (37). As described above, in this manner tip (319) is operably configured for use in procedures where marching is used. Accordingly, tip (319) is elastically deformable similar to the anvil tips shown and described in U.S. patent application Ser. No. 15/435,573 entitled "Surgical Stapler with Elastically Deformable Tip," filed on Feb. 17, 2017, published as U.S. Pub. No. 2018/0235609 on Aug. 23, 2018, the disclosure of which is incorporated by reference herein. In other examples, tip (319) may be rigid except for plug (336) as described above.

B. Tip with Tapered Insert

Figure 15:
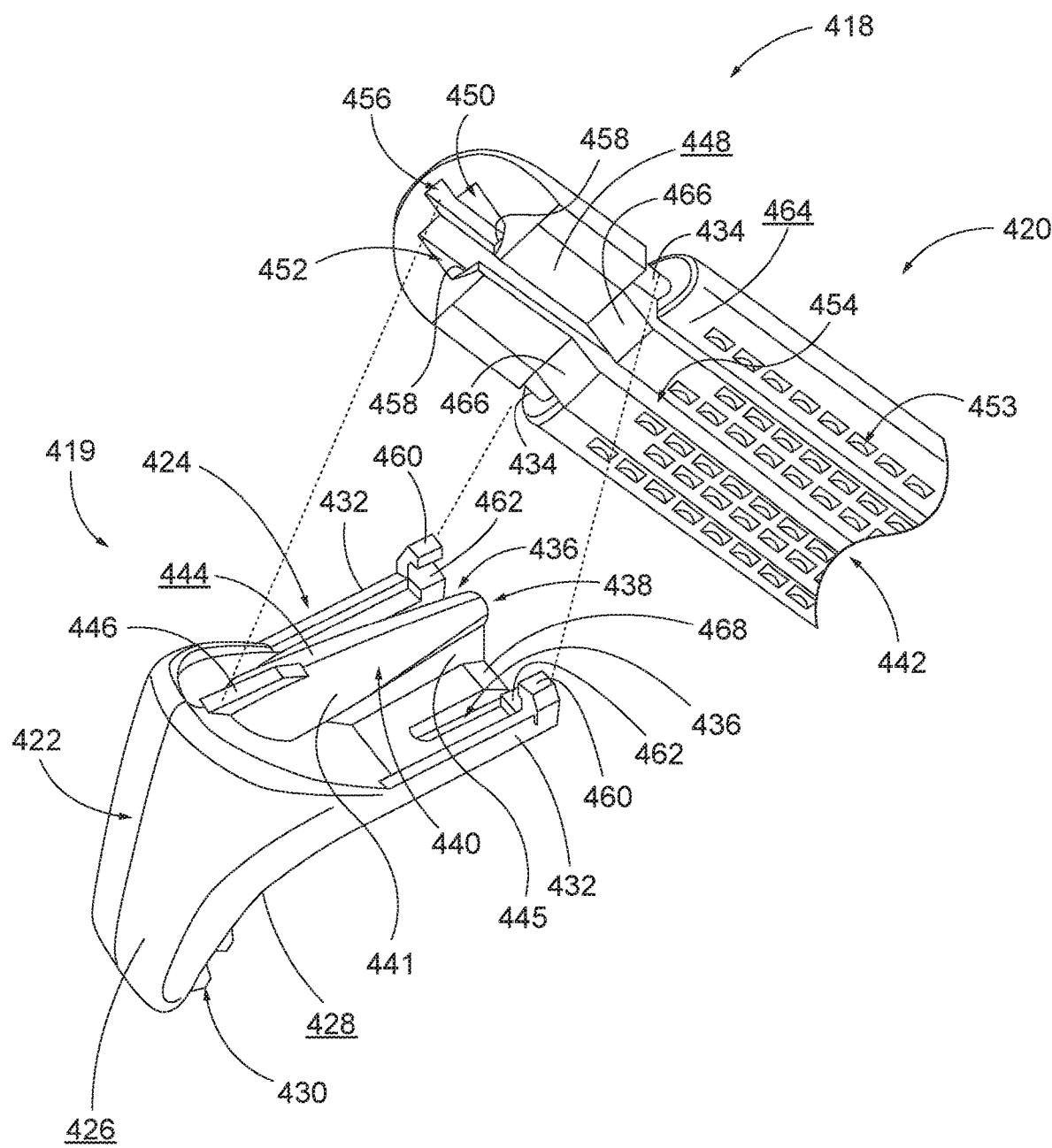
FIG. 15 depicts an enlarged exploded perspective view of a distal portion of another alternative version of an anvil of an end effector, with the anvil having a curved modular tip.

FIG. 15 shows an exemplary anvil (418) suitable for use with any of the end effectors and surgical instruments described herein. Anvil (418) comprises a tip (419) and a body (420). Tip (419) is selectively connectable with body (420) such that tip (419) is configured as a modular and releasable tip. In the illustrated version of FIG. 15, tip (419) is curved such that tip (419) extends distally from body (420) in a curved fashion where tip (419) curves or bends away from a longitudinal axis defined by body (420) downward or in the direction toward a staple cartridge of the end effector as shown and described above and that is usable with anvil (418). While shown as curved in the illustrated version, in some other versions, tip (419) can be straight such that it extends along the longitudinal axis defined by body (420).

Tip (419) comprises distal end (422) and proximal end (424). Distal end (422) is configured as an exterior portion of tip (419) that remains outside of body (420) when tip (419) is connected with body (420). Proximal end (424) has portions that are configured as an interior portion of tip (419) that is positioned within body (420) when tip (419) is connected with body (420). Distal end (422) of tip (419) further comprises a top surface (426) and a bottom surface (428). Bottom surface (428) extends through and forms part of proximal end (424). Bottom surface (428) is operably configured as a contacting surface that contacts tissue when the end effector clamps tissue.

Tip (419) further comprises ridges (430) on bottom surface (428). Ridges (430) are operably configured as a tissue gripping feature to assist with gripping tissue when the end effector is in a closed position clamping tissue. In the present example, ridges (430) are located close to the distal-most part of distal end (422), and ridges (430) extend transversely across distal end (422) such that ridges (430) generally extend in a direction perpendicular to the longitudinal axis defined by body (420) of anvil (418). While the present example shows two ridges (430), in other versions the number of ridges (430) can be greater or fewer, or ridges (430) may be omitted altogether.

Tip (419) further comprises latches (432) with one on each side of tip (419). In the illustrated version, tip (419) has two latches (432), although in other versions tip (419) can have greater or fewer latches (432). Latches (432) are located in proximal end (424) and define a portion of the outer perimeter of tip (419) in proximal end (424). Latches (432) extend proximally toward body (420). As will be described in further detail below, latches (432) are operably configured to engage with shoulders (434) formed in body (420), and such engagement provides or contributes to selectively securing tip (419) with body (420). Additionally, this engagement also provides for a way to align tip (419) with body (420).

Adjacent to each latch (432) within proximal end (424) are slots (436). Slots (436) extend from the proximal-most end of tip (419) distally within proximal end (424). Slots (436) define respective spaces between respective latches (432) and a center portion (438) of proximal end (424) of tip (419). With this configuration, latches (432) are operably configured to deflect outwardly away from center portion (438) in response to a force applied along an inside region of latches (432). Latches (432) also can deflect downwardly toward a cartridge or lower arm of the end effector instead of or in addition to deflecting outward. When not subject to a deflecting force, latches (432) are biased to return to their initial position as shown in FIG. 15.

Tip (419) further comprises insert (440) formed as part of tip (419). Insert comprises body (441). In the present example, insert (440) is formed in proximal end (424) of tip (419) and extends the length of proximal end (424). Insert (440) comprises an upper fin (446) at its distal-most end, with fin (446) extending upwardly such that fin (446) extends toward body (420) when tip (419) is connected with body (420). Insert (440) comprises a tapered shape, with its smallest dimension at the proximal-most end of insert (440) and its largest dimension at the distal-most end of insert (440). In the present example, body (441) of insert (440) comprises a curved outer surface (444), although in other versions outer surface (444) is not required to be curved. Insert (440) further comprises a lower fin (445) extending downwardly such that fin (445) extends toward a cartridge or lower arm of the end effector used with anvil (418).

Body (420) comprises a plurality of staple forming pockets (453) that are similar in structure and function to staple forming pockets (53) described above. Body (420) further comprises longitudinal anvil slot (442). Along a proximal portion of body (420), longitudinal anvil slot (442) has a T-shape portion (454) similar to longitudinal anvil slot (42) as seen in FIG. 3. Along a distal portion of body (420), however, longitudinal anvil slot (442) comprises a modified T-shaped portion (450). Modified T-shaped portion (450) comprises horizontal portion (452) intersecting with vertical portion (456). Along a bottom or lower part of horizontal portion (452) are angled surfaces (458). With this configuration, modified T-shaped portion (450) is configured to receive insert (440) of tip (419). When tip (419) is connected with body (420), vertical portion (456) of modified T-shaped portion (450) receives lower and upper fins (445, 446), while horizontal portion (452) receives body (441) of insert (440). Furthermore, the size and tapered shape of insert (440) and the size and shape of horizontal portion (452) are configured so that as insert (440) is received within modified T-shaped portion (450), the sidewalls of anvil (418) that define horizontal portion (452) will contact outer surface (444) of insert (440) to thereby retain tip (419) to body (420). With this configuration, lower and upper fins (445, 446) along with vertical portion (456) act as guide features during assembly of tip (419) with body (420).

Body (420) further comprises shoulders (434) as mentioned above. Shoulders (434) are configured with a cuboid shape with shoulders (434) being formed in body (420) as recessed portions of body (420). Shoulders (434) are further configured to be engaged by latches (432) as described above, and such engagement provides or contributes to selectively securing tip (419) with body (420). When connecting tip (419) with body (420), the sides of the distal portion of body (420) deflect latches (432) outward as insert (440) of tip (419) is inserted within modified T-shaped portion (450) and advanced proximally. Once insert (440) is sufficiently proximal within modified T-shaped portion (450), latches (432) are adjacent shoulders (434) and return to their biased state thereby moving back inwardly from their outwardly deflected state. In doing so, respective latches (432) grasp respective shoulders (434) on each side of body (420), with shoulders (434) being received within a top member (460) and bottom member (462) of each respective latch (432).

To facilitate deflection of latches (432) as described above, in the present example, the distal portion of body (420) tapers or narrows slightly. This taper of body (420) provides for ease of alignment when aligning tip (419) with body (420). As tip (419) is advanced proximally during assembly, the distal portion of body (420) becomes wider thereby contacting latches (432) and ultimately deflecting latches (432) outwardly as described above.

The distal portion of body (420) is also formed with a smaller height compared to the remainder of body (420). For instance, the distal portion of body (420) includes a bottom surface (448) that defines a plane. Also, the remainder of body (420) includes a bottom surface (464) that also defines a plane. In the present example these planes are not co-planar but they are generally parallel. The offset between these two planes represents the height difference between the distal portion of body (420) and the remainder of body (420). Furthermore, when tip (419) is connected with body (420), bottom surface (428) of tip (419) aligns with bottom surface (464) of body (420). Body (420) also comprises chamfers (466), that align with and contact chamfers (468) on each side of proximal end (424) of tip (419) when tip (419) is fully connected with body (420). In this fashion, chamfers (466, 468) act as stops.

With tip (419) inserted within, or connected with, body (420), latches (432) grasp shoulders (434), body (441) of insert (440) fits within modified T-shaped portion (450) of longitudinal anvil slot (442), and lower and upper fins (445, 446) of insert (440) fit within vertical portion (456) of modified T-shaped portion (450) of longitudinal anvil slot (442). In the present example, insert (440) is configured such that its most proximal location within modified T-shaped portion (450) remains distal to the distal-most travel of firing beam (14) as described above.

With the configuration described above, tip (419) and body (420) comprise a plurality of retaining features that are operably configured to selectively secure tip (419) with body (420). In this manner, the retaining features comprise one or more of the complementary interfaces described above. For instance, the fit of one of shoulders (434) within one of latches (332) would represent a complementary interface and thus one of the plurality of retaining features. Similarly, the fit of body (441) of insert (440) within horizontal portion (452) of modified T-shaped portion (450) of longitudinal anvil slot (442) would be another. While in the present example there are multiple retaining features configured to secure tip (419), in other versions the precise number of retaining features can be greater or fewer. Also, the precise shapes and configurations for shoulders (434), latches (432), insert (440), and slot (442) are merely exemplary. In view of the teachings herein, other shapes for and modifications to these features will be apparent to those of ordinary skill in the art.

Tip (419) is also removable from body (420) such that tip (419) may be replaced due to wear and tear, or for a different tip configuration, or for any other reason. To remove tip (419), latches (432) may be deflected either outwardly to release from shoulders (434), or latches (432) may be deflected downwardly to release from shoulders (434). With latches (432) disengaged from shoulders (434), a user may grasp distal end (422) of tip (419) and pull tip (419) distally away from body (420). With this action, insert (440) is removed from within longitudinal anvil slot (442), and tip (419) is separated from or removed from body (420). When removing tip (419) from body (420), in some versions a tool or other instrument may be used to assist in disengaging latches (432) from shoulders (434). In other versions when removing tip (419) from body (420), no tools or other instruments are required, and merely a downward or distally directed force on distal end (422) to tip (419) will cause latches (432) to disengage from shoulders (434). In view of the teachings herein, other ways to remove tip (419) will be apparent to those of ordinary skill in the art.

In the present example, tip (419) is elastically deformable such that in use, during clamping tissue for example, tip (419) may deflect or bend from a curved state to a straight or less curved state. By way of example only, tip (419) may be deflectable between about 20 degrees and about 70 degrees in a downward direction from a longitudinal axis toward cartridge; between about 0 degrees and about 90 degrees in an upward direction from a longitudinal axis toward cartridge (37). The degree of deflection may be influenced by the thickness and/or density of the tissue that is being compressed between anvil (318) and cartridge (37). As described above, in this manner tip (419) is operably configured for use in procedures where marching is used.

Accordingly, tip (419) is elastically deformable similar to the anvil tips shown and described U.S. patent application Ser. No. 15/435,573 entitled "Surgical Stapler with Elastically Deformable Tip," filed on Feb. 17, 2017, published as U.S. Pub. No. 2018/0235609 on Aug. 23, 2018, the disclosure of which is incorporated by reference herein. In other examples, tip (419) may be rigid except for latches (432) as described above.

C. Tip with Separate Tapered Shim

Figure 16:
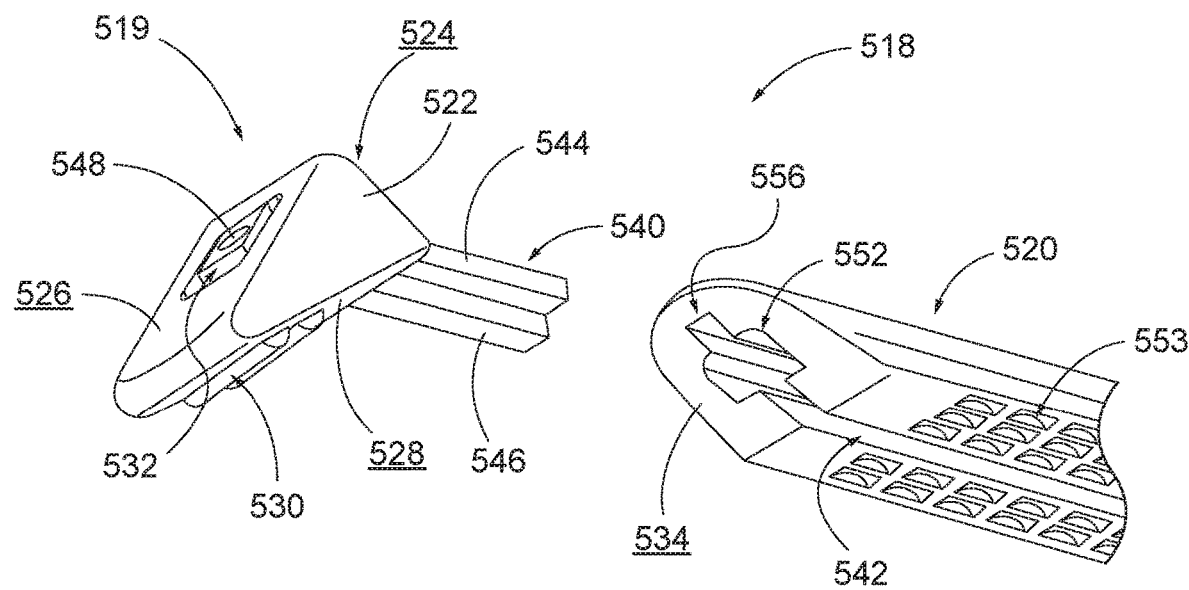
FIG. 16 depicts an enlarged exploded perspective view of a distal portion of another alternative version of an anvil of an end effector, with the anvil having a curved modular tip.

FIG. 16 shows an exemplary anvil (518) suitable for use with any of the end effectors and surgical instruments described herein. Anvil (518) comprises a tip (519), a body (520), and a shim (540). Tip (519) is selectively connectable with body (520) using shim (540) such that tip (519) is configured as a modular and releasable tip. In the illustrated version of FIG. 16, tip (519) is curved such that tip (519) extends distally from body (520) in a curved fashion where tip (519) curves or bends away from a longitudinal axis defined by body (520) downwardly or in the direction toward a staple cartridge of the end effector as shown and described above and that is usable with anvil (518). While shown as curved in the illustrated version, in some other versions, tip (519) can be straight such that it extends along the longitudinal axis defined by body (520).

In the illustrated example, tip (519) comprises an inclined or ramp shape with triangular shaped sides (522), a rear surface (524), a top surface (426), and a bottom surface (528). Bottom surface (528) is operably configured as a contacting surface that contacts tissue when the end effector clamps tissue. Tip (519) comprises opening (532) extending through tip (519) and configured to receive shim (540). Tip (519) further comprises ridges (530) on bottom surface (528). Ridges (530) are operably configured as a tissue gripping feature to assist with gripping tissue when the end effector is in a closed position clamping tissue. In the present example, ridges (530) are located close to the distal-most part of tip (519), and ridges (530) extend transversely across tip (519) such that ridges (530) generally extend in a direction perpendicular to the longitudinal axis defined by body (520) of anvil (518). While the present example shows two ridges (530), in other versions the number of ridges (530) can be greater or fewer, or ridges (530) may be omitted altogether.

Body (520) comprises a plurality of staple forming pockets (553) that are similar in structure and function to staple forming pockets (53) described above. Body (520) further comprises longitudinal anvil slot (542). Longitudinal anvil slot (542) has a T-shape profile similar to longitudinal anvil slot (42) as seen in FIG. 3. Slot (542) includes a horizontal portion (552) and an intersecting vertical portion (556) to form the T-shape. With this configuration, slot (542) is configured to receive shim (540). Body (520) further comprises front surface (534). Front surface (534) is angled such that a plane defined by front surface (534) intersects a longitudinal axis of body (520) to form an acute angle. Rear surface (524) has a matching angle such that a plane defined by rear surface (524) intersects a longitudinal axis of body (520) when tip (519) is installed with body (520) to form a matching acute angle. With this configuration, when tip (519) is fully connected with body (520), rear surface (524) of tip (519) contacts front surface (534) of body (520).

As mentioned above, opening (532) in tip (519) is configured to receive shim (540). Within opening (532) is a limiting feature that prevents shim (540) from freely passing entirely through opening (532) from one side to the other. In one example this limiting feature comprises a smaller width for opening (532) compared to the maximum width of shim (540). Other limiting features will be apparent to those of ordinary skill in the art in view of the teachings herein.

Slot (542) of body (520) is also configured to receive shim (540). In the present example, shim (540) comprises a lateral portion (544) on each side and a center portion (546) between lateral portions (544). When shim (540) is inserted within slot (542), lateral portions (544) are received within horizontal portion (552) of slot (542), while center portion (546) is received within vertical portion (556) of slot (542). In the present example, shim (540) is configured such that its most proximal location within longitudinal anvil slot (542) remains distal to the distal-most travel of firing beam (14) as described above.

In the present example, for ease of assembly, and for retention of tip (519) to body (520), shim (540) has a tapered configuration where shim (540) tapers from wider at its distal end to narrower at its proximal end. The size of shim (540) at its wider distal end is configured such that it contacts the interior sidewalls of body (520) that form slot (542) when shim (540) is fully inserted within slot (542). This contact creates an impingement or interference between shim (540) and body (520). With shim (540) extending through opening (532) in tip (519), and then through slot (542), the impingement or contact between shim (540) and body (520) operate to selectively retain tip (519) within body (520). In some versions, shim (540) is constructed of a elastomeric material that is compressible yet resilient. In such versions, shim (540) may be compressed to some degree when inserted within slot (542), and such compression may promote selective and secure retention of shim (540) within slot (542).

Shim (540) further comprises recess (548) at its distal end. Recess (548) is configured for receiving a driver tool that may be used to position and place shim (540) through opening (532) in tip (519) and ultimately into slot (542) of body (520). With shim (540) positioned through opening (532) and within slot (542), the driver tool can be used to advance shim (540) proximally up until rear surface (524) of tip (519) contacts front surface (534) of body (520) and shim (540) is securely seated within slot (542). In some other versions or applications, placement and/or insertion of shim (540) can occur without the use of a driver tool. In some such examples, recess (548) may be omitted as well. In view of the teaching herein, other ways to use and attach a modular releasable tip, such as tip (519), to a body of an anvil, such as body (520) of anvil (518), will be apparent to those of ordinary skill in the art.

Tip (519) is also removable from body (520) such that tip (519) may be replaced due to wear and tear, or for a different tip configuration, or for any other reason. To remove tip (519), the end effector is moved to an open position such that longitudinal anvil slot (542) is accessible. The driver tool or other blunt instrument can be inserted within a proximal portion of slot (542) proximal to shim (540). The tool or instrument can then be advanced distally to contact the end of shim (540) and push it distally to remove shim (540) from slot (542). With shim (540) removed from slot (542) tip (519) is no longer secured to body (520) and tip (519) can be removed and replaced if desired. In view of the teachings herein, other ways to remove tip (519) will be apparent to those of ordinary skill in the art.

In the present example, tip (519) is elastically deformable such that in use, during clamping tissue for example, tip (519) may deflect or bend from a curved state to a straight or less curved state. As described above, in this manner tip (519) is operably configured for use in procedures where marching is used. Accordingly, tip (519) is elastically deformable similar to the anvil tips shown and described in U.S. patent application Ser. No. 15/435,573 entitled "Surgical Stapler with Elastically Deformable Tip," filed on Feb. 17, 2017, published as U.S. Pub. No. 2018/0235609 on Aug. 23, 2018, the disclosure of which is incorporated by reference herein. In other examples, tip (519) may be rigid.

Figure 17:
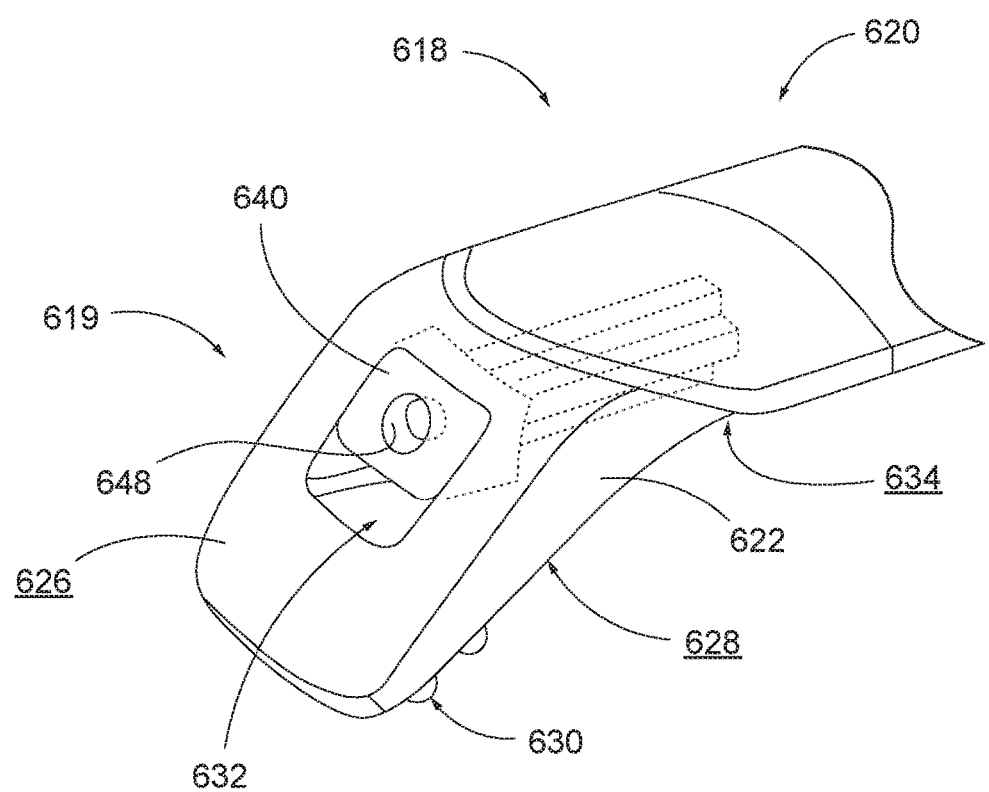
FIG. 17 depicts an enlarged perspective view of a distal portion of another alternative version of an anvil of an end effector, with the anvil having a curved modular tip.
Figure 18:
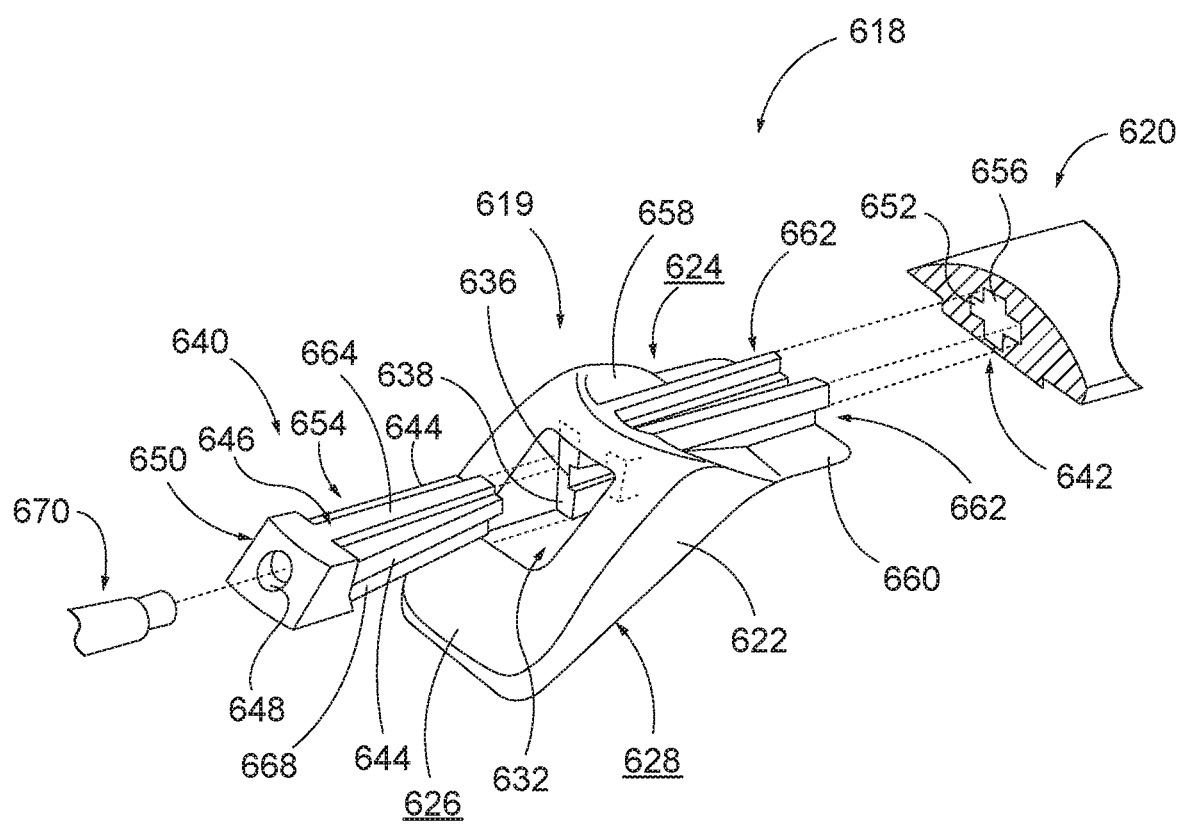
FIG. 18 depicts an exploded perspective view of the distal portion of the anvil of FIG. 17, shown with a body portion of the anvil in cross section to reveal a longitudinal slot.

FIGS. 17 and 18 show exemplary anvil (618) suitable for use with any of the end effectors and surgical instruments described herein. Anvil (618) comprises a tip (619), a body (620), and a shim (640). Tip (619) is selectively connectable with body (620) using shim (640) such that tip (619) is configured as a modular and releasable tip. In the illustrated version, tip (619) is curved such that tip (619) extends distally from body (620) in a curved fashion where tip (619) curves or bends away from a longitudinal axis defined by body (620) downwardly or in the direction toward a staple cartridge of the end effector as shown and described above and that is usable with anvil (618). While shown as curved in the illustrated version, in some other versions, tip (619) can be straight such that it extends along the longitudinal axis defined by body (620).

In the illustrated example, tip (619) comprises an inclined or ramp shape with triangular shaped sides (622), a rear surface (624), a top surface (626), and a bottom surface (628). Bottom surface (628) is operably configured as a contacting surface that contacts tissue when the end effector clamps tissue. Tip (619) further comprises ridges (630) on bottom surface (628). Ridges (630) are operably configured as a tissue gripping feature to assist with gripping tissue when the end effector is in a closed position clamping tissue. In the present example, ridges (630) are located close to the distal-most part of tip (619), and ridges (630) extend transversely across tip (619) such that ridges (630) generally extend in a direction perpendicular to the longitudinal axis defined by body (620) of anvil (618). While the present example shows two ridges (630), in other versions the number of ridges (630) can be greater or fewer, or ridges (630) may be omitted altogether.

Tip (619) comprises opening (632) extending through tip (619) and configured to receive shim (640). Within opening (632) are slots (636), with one slot (636) extending along each side of opening (632). Slots (636) are configured to receive lateral portions (644) of shim (640). Limiting members (638) are also within opening (632) and are configured as stops such that shim (640) is prevented from passing completely through opening (632). For instance, shim (640) comprises head portion (650) and tail portion (654), which extends proximally from the proximal side of head portion (650). Head portion (650) is wider than tail portion (654) such that a proximal surface of head portion (650) contacts limiting members (638) when shim (640) is fully inserted within opening (632).

Referring to FIG. 18, rear surface (624) of tip (619) comprises angled portion (658) and straight portion (660). Extending proximally from angled portion (658) are extension members (662). Extension members (662) are configured to be received within a T-shaped longitudinal anvil slot (642). Between extension members (662) is a proximal side of opening (632). In the present example extension members (662) are resiliently biased such that they may deflect outwardly away from opening (632) in response to an outward force being applied to extension members (662). For instance, when shim (640) is inserted through opening (632), lateral portions (644) of shim (640) are guided through slots (636) and extend through the proximal side of opening (632), where lateral portions (644) of shim (640) contact extension members (662). As shim (640) is advanced further proximally, lateral portions (644) of shim (640) push outwardly on extension members (662), which causes extension members (662) to resiliently deflect outwardly.

In the present example, shim (640) is tapered such that tail portion (654) of shim (640) becomes smaller in width and height dimensions as tail portion (654) extends proximally. Thus, the widest and tallest parts of tail portion (654) are at the distal-most end of tail portion (654) where tail portion (654) connects with head portion (650). The taper feature of shim (640) can act as an alignment feature to help position and align tip (619), shim (640), and body (620) prior to securing them together. As mentioned above, tail portion (654) of shim (640) comprises lateral portions (644). Additionally, tail portion (654) comprises a center portion (646), which extends vertically such that center portion (646) comprises an upper member (664) and a lower member (668) that are configured to be received within a vertical portion (656) of longitudinal anvil slot (642).

Shim (640) further comprises recess (648) at its distal end. Recess (648) is configured for receiving a driver tool (670) that may be used to position and place shim (640) through opening (632) in tip (619) and ultimately into slot (642) of body (620). With shim (640) positioned through opening (632) and within slot (642), the driver tool can be used to advance shim (640) proximally up until rear surface (624) of tip (619) contacts a front surface (634) of body (620) and shim (640) is securely seated within slot (642). In some other versions or applications, placement and/or insertion of shim (640) can occur without the use of a driver tool. In some such examples, recess (648) may be omitted as well. In view of the teaching herein, other ways to use and attach a modular releasable tip, such as tip (619), to a body of an anvil, such as body (620) of anvil (618), will be apparent to those of ordinary skill in the art.

Body (620) comprises a plurality of staple forming pockets (not shown) similar in structure and function to staple forming pockets (53) described above. Body (620) further comprises longitudinal anvil slot (642) as mentioned above. Longitudinal anvil slot (642) has a T-shape profile similar to longitudinal anvil slot (42) as seen in FIG. 3. Slot (642) includes a horizontal portion (652) and intersecting vertical portion (656) as mentioned above, which together form the T-shape. With this configuration, slot (642) is configured to receive shim (640) as described above. Body (620) further comprises front surface (634) as mentioned above. Front surface (634) is angled, similar to front surface (534) of FIG. 16, such that a plane defined by front surface (634) intersects a longitudinal axis of body (620) to form an acute angle. Rear surface (624) of tip (619) has a matching angle such that a plane defined by rear surface (624) intersects a longitudinal axis of body (620) when tip (619) is installed with body (620) to form a matching acute angle. With this configuration, when tip (619) is fully connected with body (620), rear surface (624) of tip (619) contacts front surface (634) of body (620).

Body (620) is further similar to body (420) of anvil (418) of FIG. 15 in that a distal portion of a bottom surface (not shown) of body (620) is recessed slightly. Thus, when tip (619) is connected with body (620), straight portion (660) of tip (619) is received within this recessed region of the bottom surface of body (620) such that bottom surface (628) of tip (619) along straight portion (660) meets flush with the remaining bottom surface of body (620) that is not recessed. In this manner, when tip (619) is connected with body (620) there is a smooth transition along the bottom surface.

When assembling anvil (618), in one exemplary process, extension members (662) are inserted within T-shaped longitudinal anvil slot (642). Shim (640) is then inserted through opening (632) and advanced proximally until head portion (650) contacts limiting members (638) within opening (632). Tail portion (654) extends out from opening (632) with lateral portions (644) contacting extension members (662) situated within longitudinal slot (642). Center portion (646) of shim (640) is received within vertical portion of slot (642). With the tapered configuration of shim (640), as shim (640) is advanced further proximally, shim (640) pushes against extension members (662), which in turn deflect outwardly and push against sidewalls of anvil (618) that define longitudinal anvil slot (642). In a similar fashion, upper member (664) and lower member (668) push against sidewalls of anvil (618) that define vertical portion (656) of slot (642). This force exerted by shim (640) increases as shim (640) is driven or advanced further proximally due to the tapered configuration of shim (640). With shim (640) full inserted or seated within tip (619) and body (620), tip (619) is selectively securely connected with body (620). In the present example, shim (640) is configured such that its most proximal location within longitudinal anvil slot (642) remains distal to the distal-most travel of firing beam (14) as described above.

In some versions, shim (640) may be constructed of an elastomeric material that is compressible yet resilient. In such versions, shim (640) may be compressed to some degree when inserted within slot (642), and such compression may further promote selective and secure retention of shim (640) within slot (642). In some other exemplary processes for connecting tip (619) with body (620), shim (640) may be connected with tip (619) first and then the combined tip (619) and shim (640) then connected or attached with body (620). In view of the teachings herein, other ways to assemble tip (619) with body (620) using shim (640) will be apparent to those of ordinary skill in the art.

Tip (619) is also removable from body (620) such that tip (619) may be replaced due to wear and tear, or for a different tip configuration, or for any other reason. To remove tip (619), the end effector is moved to an open position such that longitudinal anvil slot (642) is accessible. The driver tool or other blunt instrument can be inserted within a proximal portion of slot (642) proximal to shim (640). The tool or instrument can then be advanced distally to contact the end of shim (640) and push it distally to remove shim (640) from slot (642). With shim (640) removed from slot (642) tip (619) is no longer secured to body (620) and tip (619) can be removed and replaced if desired. In view of the teachings herein, other ways to remove tip (619) will be apparent to those of ordinary skill in the art.

In the present example, tip (619) is elastically deformable such that in use, during clamping tissue for example, tip (619) may deflect or bend from a curved state to a straight or less curved state. By way of example only, tip (619) may be deflectable between about 20 degrees and about 70 degrees in a downward direction from a longitudinal axis toward cartridge; between about 0 degrees and about 90 degrees in an upward direction from a longitudinal axis toward cartridge (37). The degree of deflection may be influenced by the thickness and/or density of the tissue that is being compressed between anvil (318) and cartridge (37). As described above, in this manner tip (619) is operably configured for use in procedures where marching is used. Accordingly, tip (619) is elastically deformable similar to the anvil tips shown and described in U.S. patent application Ser. No. 15/435,573 entitled "Surgical Stapler with Elastically Deformable Tip," filed on Feb. 17, 2017, published as U.S. Pub. No. 2018/0235609 on Aug. 23, 2018, the disclosure of which is incorporated by reference herein. In other examples, tip (619) may be rigid.

The several examples of modular tips shown and described herein are presented as modular tips for connection with an anvil of an end effector. In these examples the anvil is the movable jaw portion of the end effector while the cartridge is the fixed or non-movable jaw portion of the end effector. Thus, the modular tips shown and described herein are attachable or connectable with the movable jaw portion of an end effector. However, in other versions, the modular tips described herein can be adapted or modified to be tips for the cartridge or non-movable jaw portion of the end effector. Such modifications to the tips and cartridge or lower jaw of the end effector will be apparent to those of ordinary skill in the art in view of the teachings herein. It should also be understood that, in some variations of instrument (10), the anvil may remain stationary relative to the shaft assembly while the jaw portion holding the staples pivots toward and away from the fixed anvil.

In some versions of the tips shown and described herein, a special tool or cartridge can be adapted for use to assist in inserting the tips and removing the tips. In some instances the tool or cartridge may be configured for inserting and/or removing only the tip of the anvil, while in other instances the tool or cartridge may be configured for inserting and/or removing both the tip of the anvil and a staple cartridge as well. Some exemplary such tools or cartridges for inserting and/or removing anvil tips and lower arm cartridges are shown and described in U.S. patent application Ser. No. 15/435,618, entitled "Surgical Stapler with Cooperating Distal Tip Features on Anvil and Staple Cartridge," filed on Feb. 17, 2017, published as U.S. Pub. No. 2018/0235611 on Aug. 23, 2018, the disclosure of which is incorporated by reference herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a body; (b) a shaft extending from the body, wherein the shaft defines a longitudinal axis; and (c) an end effector in communication with the shaft, wherein the end effector is operable to compress, staple, and cut tissue, wherein the end effector comprises: (i) a lower arm configured to hold a staple cartridge, (ii) an anvil body movable between an open position and a closed position, and (iii) a curved anvil tip, wherein the curved anvil tip is configured to be selectively secured with a distal end of the anvil body, wherein the curved anvil tip is elastically deformable and configured to deflect in response to tissue captured between the curved anvil tip and a the lower arm as the anvil body moves toward the closed position.

Example 2

The apparatus of Example 1, wherein the anvil body comprises a longitudinal slot, wherein at least a portion of the curved anvil tip is received within a portion of the longitudinal slot when the curved anvil tip is selectively secured to the anvil body.

Example 3

The apparatus of any one or more of Examples 1 through 2, wherein the curved anvil tip comprises one or more ridges operatively configured for gripping tissue.

Example 4

The apparatus of any one or more of Examples 1 through 3, wherein the curved anvil tip comprises an insert configured to fit within a distal portion of a longitudinal slot formed in the anvil body.

Example 5

The apparatus of Example 4, wherein the insert is tapered.

Example 6

The apparatus of any one or more of Examples 4 through 5, wherein the insert is configured to elongate in response to a pulling force applied to the insert.

Example 7

The apparatus of any one or more of Examples 4 through 6, wherein the distal portion of the longitudinal slot comprises a T-shape having a horizontal portion and a vertical portion that intersect to form the T-shape.

Example 8

The apparatus of any one or more of Examples 1 through 7, wherein the anvil body comprises a longitudinal slot, wherein the longitudinal slot comprises a first portion at a distal end of the longitudinal slot, a second portion connected with the first portion and extending proximally from the first portion, and a third portion connected with and extending proximally from the second portion.

Example 9

The apparatus of Example 8, wherein the first portion of the longitudinal slot comprises a V-shaped portion.

Example 10

The apparatus of any one or more of Examples 8 through 9, wherein the second portion of the longitudinal slot comprises a cylindrical shaped portion.

Example 11

The apparatus of any one or more of Examples 8 through 10, wherein the curved anvil tip comprises a neck portion, a plug, and a guide feature.

Example 12

The apparatus of Example 11, wherein the neck portion of the curved anvil tip is configured to be received and selectively retained within the first portion of the longitudinal slot, wherein the plug is configured to be received and selectively retained within the second portion of the longitudinal slot, and wherein the guide feature is configured to be received and selectively retained within the third portion of the longitudinal slot.

Example 13

The apparatus of any one or more of Examples 1 through 12, wherein the anvil body comprises a longitudinal slot, wherein the longitudinal slot comprises a portion configured to receive a cylindrical insert of the anvil tip.

Example 14

The apparatus of Example 13, wherein the cylindrical insert is resilient and configured to elongate in response to a force applied to the cylindrical insert, and wherein the anvil body is configured such that selectively securing the anvil tip with the anvil body requires elongating the cylindrical insert to place the cylindrical insert within the portion of the longitudinal slot configured to receive the cylindrical insert.

Example 15

The apparatus of any one or more of Examples 1 through 14, wherein the anvil body comprises a first alignment feature, wherein the curved anvil tip comprises a second alignment feature, and wherein the first and second alignment features cooperate to align the curved anvil tip with the anvil body.

Example 16

An apparatus, comprising: (a) a body; (b) a shaft extending from the body, wherein the shaft defines a longitudinal axis; and (c) an end effector in communication with the shaft, wherein the end effector is operable to compress, staple, and cut tissue, wherein the end effector comprises: (i) a lower arm configured to hold a staple cartridge, (ii) an anvil body movable between an open position and a closed position, wherein the anvil body comprises a longitudinal slot, and (iii) a curved anvil tip, wherein the curved anvil tip is configured to be selectively secured with a distal end of the anvil body, wherein the curved anvil tip comprises an insert configured to be received within the longitudinal slot of the anvil body, and wherein the curved anvil tip is elastically deformable and configured to deflect in response to a clamping force applied to the curved anvil tip.

Example 17

The apparatus of Example 16, wherein the anvil body further comprises a shoulder, and wherein the curved anvil tip comprises a latch configured to selectively engage the shoulder to selectively secure the curved anvil tip with the anvil body.

Example 18

The apparatus of any one or more of Examples 16 through 17, wherein the anvil body comprises a first bottom surface, a chamfer, and a second bottom surface, wherein the first bottom surface and the second bottom surface are offset from one another.

Example 19

An apparatus, comprising: (a) a body; (b) a shaft extending from the body, wherein the shaft defines a longitudinal axis; and (c) an end effector in communication with the shaft, wherein the end effector is operable to compress, staple, and cut tissue, wherein the end effector comprises: (i) a lower arm configured to hold a staple cartridge, (ii) an anvil body movable between an open position and a closed position, wherein the anvil body comprises a longitudinal slot, (iii) a curved anvil tip, wherein the curved anvil tip is configured to be selectively secured with a distal end of the anvil body, wherein the curved anvil tip is elastically deformable and configured to deflect in response to a clamping force applied to the curved anvil tip, and wherein the curved anvil tip comprises an opening extending from a distal end of the curved anvil tip to a proximal end of the curved anvil tip, and (iv) a tapered shim configured to be received within and extend through the opening of the curved anvil tip, wherein the shim further extends within a portion of the longitudinal slot of the anvil body, and wherein the shim is configured such that engagement between the shim and the longitudinal slot of the anvil body selectively secures the curved anvil tip with the anvil body.

Example 20

The apparatus of Example 19, wherein the curved anvil tip further comprises an extension member that extends proximally from a rear surface of the curved anvil tip, wherein the extension member is configured to be received within the longitudinal slot of the anvil body, and wherein the shim is configured to apply an outward force on the extension member when the shim extended within the longitudinal slot.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that the teachings herein may be readily combined with various teachings in U.S. patent application Ser. No. 29/594,332, entitled "Surgical Stapler End Effector with Varying Deck Height and Tissue Gripping Features," filed on even date herewith, the disclosure of which is incorporated by reference herein. Various suitable ways in which the teachings herein may be combined with the teachings of U.S. patent application Ser. No. 29/594,332 will be apparent to those of ordinary skill in the art.

It should also be understood that the teachings herein may be readily combined with various teachings in U.S. patent application Ser. No. 29/594,335, entitled "Circular Surgical Stapler End Effector with Varying Deck Height and Tissue Gripping Features," filed on even date herewith, the disclosure of which is incorporated by reference herein. Various suitable ways in which the teachings herein may be combined with the teachings of U.S. patent application Ser. No. 29/594,335 will be apparent to those of ordinary skill in the art.

It should also be understood that the teachings herein may be readily combined with various teachings in U.S. patent application Ser. No. 15/435,573, entitled "Surgical Stapler with Elastically Deformable Tip," filed on even date herewith, the disclosure of which is incorporated by reference herein. Various suitable ways in which the teachings herein may be combined with the teachings of U.S. patent application Ser. No. 15/435,573 will be apparent to those of ordinary skill in the art.

It should also be understood that the teachings herein may be readily combined with various teachings in U.S. patent application Ser. No. 15/435,618, entitled "Surgical Stapler with Cooperating Distal Tip Features on Anvil and Staple Cartridge," filed on even date herewith, the disclosure of which is incorporated by reference herein. Various suitable ways in which the teachings herein may be combined with the teachings of U.S. patent application Ser. No. 15/435,618 will be apparent to those of ordinary skill in the art.

It should also be understood that the teachings herein may be readily combined with various teachings in U.S. patent application Ser. No. 29/594,340, entitled "Surgical Stapler with Bent Anvil Tip and Angled Staple Cartridge Tip," filed on even date herewith, the disclosure of which is incorporated by reference herein. Various suitable ways in which the teachings herein may be combined with the teachings of U.S. patent application Ser. No. 29/594,340 will be apparent to those of ordinary skill in the art.

It should also be understood that the teachings herein may be readily combined with various teachings in U.S. patent application Ser. No. 15/435,631, entitled "Surgical Stapler with Bent Anvil Tip, Angled Staple Cartridge Tip, and Tissue Gripping Features," filed on even date herewith, the disclosure of which is incorporated by reference herein. Various suitable ways in which the teachings herein may be combined with the teachings of U.S. patent application Ser. No. 15/435,631 will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, the disclosure of which is incorporated by reference herein; U.S. Pub. No. 2012/0199630, entitled "Robotically-Controlled Surgical Instrument with Force-Feedback Capabilities," published Aug. 9, 2012, the disclosure of which is incorporated by reference herein; U.S. Pub. No. 2012/0132450, entitled "Shiftable Drive Interface for Robotically-Controlled Surgical Tool," published May 31, 2012, the disclosure of which is incorporated by reference herein; U.S. Pub. No. 2012/0199633, entitled "Surgical Stapling Instruments with Cam-Driven Staple Deployment Arrangements," published Aug. 9, 2012, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, the disclosure of which is incorporated by reference herein; U.S. Pub. No. 2012/0199632, entitled "Robotically-Controlled Surgical Instrument with Selectively Articulatable End Effector," published Aug. 9, 2012, the disclosure of which is incorporated by reference herein; U.S. Pub. No. 2012/0203247, entitled "Robotically-Controlled Surgical End Effector System," published Aug. 9, 2012, the disclosure of which is incorporated by reference herein; U.S. Pub. No. 2012/0211546, entitled "Drive Interface for Operably Coupling a Manipulatable Surgical Tool to a Robot," published Aug. 23, 2012; U.S. Pub. No. 2012/0138660, entitled "Robotically-Controlled Cable-Based Surgical End Effectors," published Jun. 7, 2012, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination.

Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a body;
   (b) a shaft extending from the body, wherein the shaft defines a longitudinal axis; and
   (c) an end effector in communication with the shaft, wherein the end effector is operable to compress, staple, and cut tissue, wherein the end effector comprises:
      (i) a lower jaw configured to hold a staple cartridge,
      (ii) an anvil body movable relative to the lower jaw between an open position and a closed position, wherein the anvil body includes a distal face and a longitudinal slot that opens distally through the distal face, wherein the longitudinal slot includes:
         (A) a V-shaped first portion at a distal end of the longitudinal slot,
         (B) a second portion connected with the first portion and extending proximally from the first portion, and
         (C) a third portion connected with and extending proximally from the second portion,
      (iii) a translatable member slidably received by the longitudinal slot, wherein the translatable member is selectively actuatable through the longitudinal slot between a proximal position and a distal position when the anvil body is in the closed position, and
      (iv) a curved anvil tip configured to be selectively coupled with a distal end of the anvil body, wherein a proximal portion of the curved anvil tip includes a proximal face and a tapered projection extending proximally from the proximal face, wherein the proximal face is configured to abut the distal face of the anvil body and the tapered projection is configured to be received through the distal face and into the longitudinal slot, wherein the curved anvil tip is configured to resiliently deflect away from the lower jaw in response to tissue being captured between the curved anvil tip and the lower jaw as the anvil body moves toward the closed position.

2. The apparatus of claim 1, wherein the curved anvil tip comprises one or more ridges operatively configured for gripping tissue.

3. The apparatus of claim 1, wherein the projection is configured to elongate in response to a pulling force applied to the projection by a tool.

4. The apparatus of claim 1, wherein a portion of the longitudinal slot comprises a T-shape having a horizontal portion and a vertical portion that intersect to form the T-shape.

5. The apparatus of claim 1, wherein the second portion of the longitudinal slot comprises a cylindrical shaped portion.

6. The apparatus of claim 1, wherein the projection comprises a neck portion, a plug extending proximally from the neck portion, and a guide feature extending proximally from the plug.

7. The apparatus of claim 6, wherein the neck portion of the projection is configured to be received and selectively retained within the first portion of the longitudinal slot, wherein the plug is configured to be received and selectively retained within the second portion of the longitudinal slot, and wherein the guide feature is configured to be received and selectively retained within the third portion of the longitudinal slot.

8. The apparatus of claim 1, wherein the projection includes a cylindrical portion, and wherein the longitudinal slot comprises a portion configured to receive the cylindrical portion for coupling the anvil body with the curved anvil tip.

9. The apparatus of claim 8, wherein the cylindrical portion of the projection is resilient and configured to elongate in response to a force applied to the cylindrical portion, and wherein the anvil body is configured such that selectively securing the curved anvil tip with the anvil body requires elongating the cylindrical portion to place the cylindrical portion within the portion of the longitudinal slot configured to receive the cylindrical portion.

10. The apparatus of claim 1, wherein the anvil body comprises a first alignment feature, wherein the curved anvil tip comprises a second alignment feature, and wherein the first and second alignment features cooperate to align the curved anvil tip with the anvil body.

11. The apparatus of claim 1, wherein the translatable member comprises a cutting element operable to cut tissue captured between the lower jaw and the anvil body in the closed position.

12. The apparatus of claim 1, wherein the projection includes a tool engagement opening configured to receive a tool to facilitate coupling of the curved anvil tip with the anvil body, wherein the tool engagement opening is accessible through a tissue clamping surface of the anvil body via the longitudinal slot when the curved anvil tip is coupled to the anvil body.

13. The apparatus of claim 1, wherein the distal face of the anvil body includes a first retaining feature, wherein the proximal face of the curved anvil tip includes a second retaining feature configured to engage the first retaining feature to retain the curved anvil tip axially relative to the anvil body.

14. The apparatus of claim 1, wherein the anvil body further comprises a shoulder, and wherein the curved anvil tip comprises a latch configured to selectively engage the shoulder to selectively secure the curved anvil tip with the anvil body.

15. An apparatus, comprising:
   (a) a body;
   (b) a shaft extending from the body, wherein the shaft defines a longitudinal axis; and
   (c) an end effector in communication with the shaft, wherein the end effector is operable to compress, staple, and cut tissue, wherein the end effector comprises:
      (i) a lower jaw configured to hold a staple cartridge,
      (ii) an anvil body movable relative to the lower jaw between an open position and a closed position for clamping tissue therebetween, wherein the anvil body comprises a longitudinal slot extending parallel to the longitudinal axis, wherein the longitudinal slot includes an open distal slot end and a widened slot portion proximal to the open distal slot end, and
      (iii) a curved anvil tip, wherein the curved anvil tip is configured to be selectively secured with a distal end of the anvil body, wherein the curved anvil tip comprises a proximal face and a projection extending proximally from the proximal face, wherein the projection is configured to be received proximally through the open distal slot end and into the widened slot portion, and wherein the projection includes a tool engagement feature that is accessible through the widened slot portion by a tool for selectively securing the curved anvil tip with the distal end of the anvil body,
   wherein the projection has a larger width than the open distal slot end,
   wherein the projection is configured to resiliently compress in response to engagement of a tool with the tool engagement feature and thereby permit insertion of the projection proximally through the open distal slot end and into the widened slot portion,
   wherein the projection is configured to resiliently expand within the widened slot portion upon removal of the tool from the tool engagement feature and thereby secure the curved anvil tip to the anvil body,
   wherein the curved anvil tip is elastically deformable and configured to deflect in response to a clamping force applied to the curved anvil tip.

16. The apparatus of claim 15, wherein the anvil body further comprises a shoulder, and wherein the curved anvil tip comprises a latch configured to selectively engage the shoulder to selectively secure the curved anvil tip with the anvil body.

17. The apparatus of claim 15, wherein the anvil body comprises a first bottom surface, a chamfer, and a second bottom surface, wherein the first bottom surface and the second bottom surface are offset from one another.

18. The apparatus of claim 15, wherein the anvil further includes a tissue contacting surface having a plurality of staple forming pockets, wherein the widened slot portion opens through the tissue contacting surface.

19. An apparatus, comprising:
   (a) a body;
   (b) a shaft extending from the body, wherein the shaft defines a longitudinal axis; and
   (c) an end effector in communication with the shaft, wherein the end effector is operable to compress, staple, and cut tissue, wherein the end effector comprises:
      (i) a lower jaw configured to hold a staple cartridge,
      (ii) an anvil body movable between an open position and a closed position, wherein the anvil body comprises a longitudinal slot extending parallel to the longitudinal axis,
      (iii) a curved anvil tip, wherein the curved anvil tip is configured to be selectively secured with a distal end of the anvil body, wherein the curved anvil tip is elastically deformable and configured to deflect in response to a clamping force applied to the curved anvil tip, and wherein the curved anvil tip comprises an opening extending parallel to the longitudinal axis from a distal end of the curved anvil tip to a proximal end of the curved anvil tip, wherein the opening is configured to align coaxially with the longitudinal slot when the curved anvil tip is secured to the distal end of the anvil body, and
      (iv) a tapered shim configured to be received within and extend proximally through the opening of the curved anvil tip and a distal portion of the longitudinal slot of the anvil body, and wherein the tapered shim is configured such that engagement between the tapered shim and the longitudinal slot of the anvil body selectively secures the curved anvil tip with the anvil body.

20. The apparatus of claim 19, wherein the tapered shim includes a distal head that defines a maximum lateral width of the tapered shim, wherein the opening of the curved anvil tip is configured to receive the distal head therein.

* * * * *